United States Patent
Ballard et al.

(10) Patent No.: US 9,932,335 B2
(45) Date of Patent: Apr. 3, 2018

(54) PYRROLOPYRIDINE OR PYRAZOLOPYRIDINE DERIVATIVES

(71) Applicant: Hoffmann-La Roche Inc., Little Falls, NJ (US)

(72) Inventors: Theresa Maria Ballard, Lutter (FR); Emmanuel Pinard, Linsdorf (FR); Herve Schaffhauser, Habsheim (FR); Katrin Groebke Zbinden, Liestal (CH); Thomas Ryckmans, Rosenau (FR); Alexander Flohr, Loerrach (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 25 days.

(21) Appl. No.: 15/068,096

(22) Filed: Mar. 11, 2016

(65) Prior Publication Data
US 2016/0194321 A1    Jul. 7, 2016

Related U.S. Application Data

(63) Continuation of application No. PCT/EP2014/068114, filed on Aug. 27, 2014.

(30) Foreign Application Priority Data

Aug. 30, 2013   (EP) .................................... 13182351

(51) Int. Cl.
  *C07D 471/04*    (2006.01)
(52) U.S. Cl.
  CPC .................. *C07D 471/04* (2013.01)
(58) Field of Classification Search
  CPC .................................................. C07D 471/04
  See application file for complete search history.

(56) References Cited

U.S. PATENT DOCUMENTS

8,883,850 B2 * 11/2014 Beshore ................. A61K 31/16
                                                                514/336
9,163,020 B2 * 10/2015 Shirude ................ C07D 471/04
                                                                546/330

FOREIGN PATENT DOCUMENTS

| WO | 2010/019391 A1 | 2/2010 |
| WO | 2011/041143 A1 | 4/2011 |
| WO | 2013/106795 A1 | 7/2013 |
| WO | WO 2015/009525 A1 * | 1/2015 |

OTHER PUBLICATIONS

ISR for PCT/EP2014/068114.
Kuduk S.D et al., "N-Heterocyclic derived M1 positive allosteric modulators" Bioorganic & Medicinal Chemistry Letters 20(4):1334-1337 (Feb. 15, 2010).

* cited by examiner

*Primary Examiner* — Timothy R Rozof
(74) *Attorney, Agent, or Firm* — Mark D. Kafka; Genentech, Inc.

(57) ABSTRACT

The present invention relates to compounds of formula

I

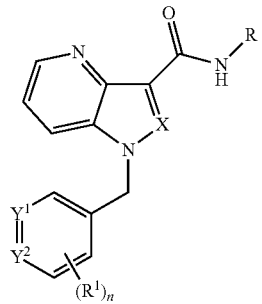

wherein $R^1$, $Y^1$, $Y^2$, X, R and n are as defined herein.

4 Claims, No Drawings

PYRROLOPYRIDINE OR PYRAZOLOPYRIDINE DERIVATIVES

CROSS-REFERENCE TO RELATED APPLICATIONS

This application is a continuation of International Application No. PCT/EP2014/068114 filed on Aug. 27, 2014, which claims priority to European Patent Application No. 13182351.0, filed on Aug. 30, 2013, the entire contents of each of which are incorporated herein by reference.

The present invention relates to compounds of formula

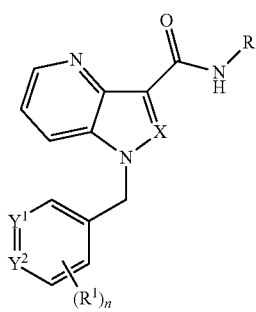

I wherein
$R^1$ halogen, lower alkyl, lower alkoxy, cyano, phenyl, C(O)NHCH$_3$, C(O)NH$_2$, lower alkyl substituted by halogen or is a five-membered heteroaryl group, optionally substituted by lower alkyl;
$Y^1$ is N or CH;
$Y^2$ is CH;
and if Y is CH, $Y^1$ and $Y^2$ may form together with the C-atoms to which they are attached a ring, containing —CH=N—N(CH$_3$)—, —CH=N—N(H)—;
X is CH or N;
R is (CH$_2$)$_m$-cycloalkyl, optionally substituted by hydroxy, lower alkoxy or lower alkyl, or is tetrahydropyran, optionally substituted by hydroxy, or is lower alkoxy, substituted by hydroxy, or is lower alkyl substituted by one or two hydroxy, or is (CH$_2$)$_m$-pyridinyl, optionally substituted by hydroxy, lower alkyl or lower alkyl substituted by hydroxy, or is L-phenyl, optionally substituted by hydroxy, lower alkyl or lower alkyl substituted by hydroxy, and
L is a bond, —CH(CH$_2$OH)— or —CH$_2$CH(OH)—;
n is 0, 1 or 2;
m is 0 or 1;
or to a pharmaceutically acceptable acid addition salt, to a racemic mixture or to its corresponding enantiomer and/or optical isomers thereof.

The compounds of the present invention are muscarinic M1 receptor positive allosteric modulators (PAM) and hence are useful in the treatment of diseases, mediated by the muscarinic M1 receptor, such as Alzheimer's disease, cognitive impairment, schizophrenia, pain or sleep disorders.

Acetylcholine (ACh) is a neurotransmitter which activates both nicotinic (ligand-gated ion channel) and muscarinic (metabotropic) receptors in the CNS and in the periphery. The muscarinic receptors (mAChRs) are members of the class A G-protein-coupled receptors. To date, five distinct subtypes of mAChRs (M1-M5) have been cloned and sequenced. The muscarinic M1 receptors are predominantly distributed in the brain, with the highest expression in the cortex, thalamus, striatum and hippocampus. In clinical studies, Xanomeline, a M1/M4-preferring agonist, demonstrated robust efficacy on positive, negative and cognitive symptoms in schizophrenic patients and improved cognitive scores and reduced psychotic-like behaviors in patients with Alzheimer's disease (AD). The M1 receptor has been implicated in memory and learning processes, regulation of dopamine and NMDA receptor activity and has thus been proposed as a potential target for the treatment of AD and schizophrenia.

AD is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length by processing of the beta-amyloid precursor protein (APP) by the beta-amyloid protein cleaving enzyme. The processing leads to accumulation of Abeta in the brain.

M1 receptors are abundantly expressed postsynaptically in cortex, hippocampus and striatum which are important brain regions involved for cognition. Based on the cholinergic hypothesis i.e. degeneration of presynaptic cholinergic nerve terminals in hippocampus and cortical regions, M1 activation should rescue the cognitive deficits which occur in AD, thus providing symptomatic treatment of this neurodegenerative disorder. Postmortem studies in AD cortical tissues have shown that M1 receptor expression are not reduced, thus providing evidence for target availability in a critical brain region. Moreover, preclinical studies have shown that M1 activation has potential as a disease-modifying therapy for AD by shifting the APP processing towards the non-amyloidogenic α-secretase pathway and by decreasing tau hyperphosphorylation. Therefore, M1 PAMs provide an approach to target both symptomatic and disease-modifying treatment of AD.

Schizophrenia is a severe, disabling, lifelong disorder that affects 1% of the population and is characterized by positive symptoms (such as hallucinations, delusions and paranoia), negative symptoms (such as social withdrawal and apathy) and cognitive impairment (for example, deficits in working memory, executive function and attention). Schizophrenia is a neurodevelopmental disorder with genetic risk factors and neuropathological changes. Aberrant activity occurs within the prefrontal-hippocampal-thalamic network in brains of schizophrenia patients. Positive symptoms of schizophrenia are suggested to be caused by dopaminergic system dysfunction, particularly increased dopamine activity within subcortical brain regions such as the striatum. Negative symptoms are thought to occur due to impaired signaling within the neurocircuitry of the ventral tegmental area and ventral striatum. Decreased NMDA receptor function in pyramidal neurons coupled with sub-optimal dopamine release in critical regions such as dorsolateral prefrontal cortex may account for some of the cognitive deficits.

M1 receptors are located in regions which are affected in schizophrenia, such as the hippocampus, cortex and striatum, in particular in the medium spiny neurons. Several reports have shown a reduction in muscarinic receptors in the prefrontal cortex and hippocampus, regions where M1 is densely expressed, in a subset of schizophrenic patients. Furthermore, preclinical studies have shown that M1 knockout mice have enhanced amphetamine-induced activity and increased striatal dopamine levels. Electrophysiology studies have revealed that activation of M1 receptors potentiates NMDA mediated hippocampal activity, modulates activity of medium spiny neurons and increases activity of medial prefrontal cortex neurons. Overall, activation of M1 receptors should modulate dysfunctional dopaminergic and glutamatergic signaling within the underlying neurocircuitry resulting in improvements in the symptoms of schizophrenia.

The clinical effects of Xanomeline and other muscarinic M1 agonist agents were however always associated with adverse effects attributed to their insufficient M1 muscarinic receptor subtype selectivity. The typical observed side effects, including sweating, salivation, gastrointestinal distress and bradycardia have been attributed to the non-specific activation of peripheral M2 and M3 mAChRs. Despite a tremendous effort from a number of companies, the search for highly M1 selective agonists has failed because of the high degree of conservation between muscarinic receptor subtypes at their orthosteric acetylcholine ligand binding sites.

To circumvent the selectivity and safety issues associated with targeting the highly conserved orthosteric ACh site, an alternative approach consists of developing M1 PAMs that act at the less highly conserved allosteric binding sites. Recently, Merck and Vanderbilt University reported M1 PAMs from different chemical classes exhibiting, as rationalized, a good level of M1 subtype selectivity Importantly, similar to the preclinical profile of Xanomeline and other unselective M1 agonists, these M1 allosteric agents demonstrated pro-cognitive effects (in scopolamine-induced memory deficit in mice, scopolamine impaired non-human primates and in transgenic AD mice). PQCA and ML169 have been shown to promote non-amyloidogenic APP processing. Electrophysiology studies have shown that M1 PAMs potentiate carbachol-induced activity in the medial prefrontal cortex and medium spiny neurons. Moreover, unlike unselective agonists, M1 PAMs do not appear to produce side effects such as salivation at therapeutic effective doses. Additionally, they are expected to be devoid of liabilities such as receptor desensitization/internalization following chronic dosing previously reported for orthosteric receptor agonists. In summary, the PAM approach, by activating in a truly selective manner M1 receptors, is a highly promising novel strategy to deliver both efficacious and safe therapeutic agents for the treatment of schizophrenia (positive, negative and cognitive symptoms) as well as AD (symptomatic and disease modifying).

Thus, the compounds of the invention, which are muscarinic M1 receptor positive allosteric modulators, are believed to be useful in the treatment of Alzheimer's disease and other diseases mediated by the muscarinic M1 receptor, without side effects.

Therefore, the object of the present invention was to identify compounds that are muscarinic M1 receptor positive allosteric modulators. It has been found that the compounds of formula I are active in this area and they may therefore be used for the treatment of Alzheimer's disease, cognitive impairment, schizophrenia, pain or sleep disorders The present invention relates to compounds of formula I and to their pharmaceutically acceptable salts, to these compounds as pharmaceutically active substances, to the processes for their production, as well as to the use in the treatment or prevention of disorders, relating to muscarinic M1 receptor positive allosteric modulators, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, isopropyl, n-butyl, i-butyl, 2-butyl, t-butyl and the like. Preferred alkyl groups with 1-4 carbon atoms.

As used therein, the term "cycloalkyl" denotes a saturated carbon ring, containing from 3 to 6 carbon ring atoms, for example cyclopropyl, cyclobutyl, cyclopentyl or cyclohexyl.

The term "alkoxy" denotes a group —O—R' wherein R' is lower alkyl as defined above.

The term "halogen" denotes chlorine, bromine, fluorine or iodine.

The term "lower alkyl substituted by halogen" denotes an alkyl group as defined above, wherein at least one hydrogen atoms is replaced by halogen, for example $CF_3$, $CH_2F$, $CH_2CF_3$, $CH_2CH_2CF_3$, $CH_2CF_2CF_3$ and the like.

The term "lower alkyl substituted by hydroxy" denotes an alkyl group as defined above, wherein at least one hydrogen atom is replaced by hydroxy, for example $CH_2OH$, $CH_2CH_2OH$, $C(CH_3)_2OH$, $CH(CH_3)CH_2OH$, $CH_2CH(OH)CH_3$, $CH_2C(OH)(CH_3)_2$, $CH(CH_2CH_3)CH_2OH$, $CH_2(CH_2OH)C(CH_3)_3$, $CH(CH_2OH)CH(CH_3)CH_2CH_3$, $CH_2CH(OH)CH_2CH_3$, $CH_2CH(OH)CH_2OH$, $CH(CH_2OH)CH(CH_3)_2$, $CH(CH_2OH)CH_2CH_2CH_3$, $CH(CH_2OH)CH_2CH(CH_3)_2$ and the like.

The term "5-membered heteroaryl group" denotes aromatic rings with 5 ring atoms, containing at least one N, S or O atom, for example thiazolyl or pyrazolyl.

The term "heteroaryl" denotes a six membered aromatic ring with 6 ring atoms, for example pyridinyl, wherein the ring-N atom may be in different positions.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like One embodiment of the present invention are compounds of formula I-A

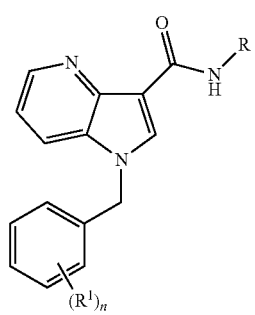

I-A wherein $R^1$ is pyrazolyl or thiazolyl, optionally substituted by lower alkyl and R is $(CH_2)_m$-cycloalkyl, optionally substituted by hydroxy, lower alkoxy or lower alkyl, and n and m are as described above, for example the following compounds 1-(2-fluoro-4-(1-methyl-1H-pyrazol-4-yl)benzyl)-N-((1S,2S)-2-hydroxycyclohexyl)-1H-pyrrolo[3,2-b]pyridine-3-carboxamide 1-(2-fluoro-4-(1-methyl-1H-pyrazol-4-yl)benzyl)-N-((1R,2R)-2-hydroxycyclohexyl)-1H-pyrrolo[3,2-b]pyridine-3-carboxamide 1-[2-fluoro-4-(1-methyl-1H-pyrazol-4-yl)-benzyl]-1H-pyrrolo[3,2-b]pyridine-3-carboxylic acid ((1R,2R)-2-hydroxy-cyclopentyl)-amide 1-[2-fluoro-4-(1-methyl-1H-pyrazol-4-yl)-benzyl]-1H-pyrrolo[3,2-b]pyridine-3-carboxylic acid ((1S,2S)-2-hydroxy-cyclopentyl)-amide 1-[2-fluoro-4-(1-methyl-1H-pyrazol-4-yl)-benzyl]-1H-pyrrolo[3,2-b]pyridine-3-carboxylic acid ((1S,2R)-2-hydroxy-cyclopentyl)-amide 1-[2-fluoro-4-(1-methyl-1H-pyrazol-4-yl)-benzyl]-1H-pyrrolo[3,2-b]pyridine-3-carboxylic acid (1-hydroxy-cyclopentylmethyl)-amide N-cyclohexyl-1-(2-fluoro-4-(1-methyl-1H-pyrazol-4-yl)benzyl)-1H-pyrrolo[3,2-b]pyridine-3-carboxamide (1-(2-fluoro-4-(1-methyl-1H-pyrazol-4-yl)benzyl)-N-((1SR,2RS)-2 hydroxycyclohexyl)-1H-pyrrolo[3,2-b]pyridine-3-carboxamide 1-[2-fluoro-4-(1-methyl-1H-pyrazol-4-yl)-benzyl]-1H-pyrrolo[3,2-b]pyridine-3-carboxylic acid ((1S,2S)-2-methoxy-cyclohexyl)-amide 1-(2-fluoro-4-(1-methyl-1H-pyrazol-4-yl)benzyl)-N-((1SR,2 SR)-2-hydroxy-2-methylcyclohexyl)-1H-pyrrolo[3,2-b]pyridine-3-carboxamide 1-(2-fluoro-4-(1-methyl-1H-pyrazol-4-yl)benzyl)-N-((1SR,2RS)-2-hydroxy-2-methylcyclohexyl)-1H-pyrrolo[3,2-b]pyridine-3-carboxamide N-((1S,2S)-2-hydroxycyclohexyl)-1-(3-(1-methyl-1H-pyrazol-4-yl)benzyl)-1H-pyrrolo[3,2-b]pyridine-3-carboxamide N-((1S,2S)-2-hydroxycyclohexyl)-1-(4-(1-methyl-1H-pyrazol-4-yl)benzyl)-1H-pyrrolo[3,2-b]pyridine-3-carboxamide 1-(2-fluoro-4-(1-methyl-1H-pyrazol-4-yl)benzyl)-N-((1SR,2 SR)-2-fluorocyclohexyl)-1H-pyrrolo[3,2-b]pyridine-3-carboxamide N-((1S,2S)-2-hydroxycyclohexyl)-1-(4-(thiazol-2-yl)benzyl)-1H-pyrrolo[3,2-b]pyridine-3-carboxamide or 1-(2-fluoro-4-(1-methyl-1H-pyrazol-4-yl)benzyl)-N-((1-hydroxycyclopropyl)methyl)-1H-pyrrolo[3,2-b]pyridine-3-carboxamide.

One further embodiment of the present invention are compounds of formula I-A, wherein R¹ is halogen, lower alkyl, lower alkoxy, cyano, phenyl, C(O)NHCH₃, C(O)NH₂, lower alkyl substituted by halogen and R is (CH₂)ₘ-cycloalkyl optionally substituted by hydroxy, lower alkoxy or lower alkyl or is tetrahydrofuran, optionally substituted by hydroxy, and n and m are as described above, for example the following compounds 1-(5-bromo-2-fluorobenzyl)-N-((1S,2S)-2-hydroxycyclohexyl)-1H-pyrrolo[3,2b]pyridine-3-carboxamide and (1S,2S)-2-aminocyclohexanol N-((1S,2S)-2-hydroxycyclohexyl)-1-(4-methylbenzyl)-1H-pyrrolo[3,2-b]pyridine-3-carboxamide 1-(3-fluoro-4-methoxybenzyl)-N-((1S,2S)-2-hydroxycyclohexyl)-1H-pyrrolo[3,2-b]pyridine-3-carboxamide 1-(4-cyanobenzyl)-N-((1S,2S)-2-hydroxycyclohexyl)-1H-pyrrolo[3,2-b]pyridine-3-carboxamide 1-(3-fluoro-4-methylbenzyl)-N-((1S,2S)-2-hydroxycyclohexyl)-1H-pyrrolo[3,2-b]pyridine-3-carboxamide N-((1S,2S)-2-hydroxycyclohexyl)-1-(4-methoxybenzyl)-1H-pyrrolo[3,2-b]pyridine-3-carboxamide 1-(biphenyl-4-ylmethyl)-N-((1S,2S)-2-hydroxycyclohexyl)-1H-pyrrolo[3,2-b]pyridine-3-carboxamide 1-(4-bromobenzyl)-N-((1S,2S)-2-hydroxycyclohexyl)-1H-pyrrolo[3,2-b]pyridine-3-carboxamide 1-(4-cyano-2-fluorobenzyl)-N-((1S,2S)-2-hydroxycyclohexyl)-1H-pyrrolo[3,2-b]pyridine-3-carboxamide 1-(4-chlorobenzyl)-N-((1S,2S)-2-hydroxycyclohexyl)-1H-pyrrolo[3,2-b]pyridine-3-carboxamide N-((1S,2S)-2-hydroxycyclohexyl)-1-(4-(methylcarbamoyl)benzyl)-1H-pyrrolo[3,2-b]pyridine-3-carboxamide 1-(4-carbamoylbenzyl)-N-((3S,4R)-3-hydroxytetrahydro-2H-pyran-4-yl)-1H-pyrrolo[3,2-b]pyridine-3-carboxamide or 1-(4-carbamoylbenzyl)-N-((3R,4S)-3-hydroxytetrahydro-2H-pyran-4-yl)-1H-pyrrolo[3,2-b]pyridine-3-carboxamide.

One further embodiment of the present invention are compounds of formula I-A, wherein R¹ is pyrazolyl, optionally substituted by lower alkyl and R is tetrahydropyran, optionally substituted by hydroxy, and n and m are as described above, for example the following compounds 1-(2-fluoro-4-(1-methyl-1H-pyrazol-4-yl)benzyl)-N-((3RS,4SR)-3-hydroxytetrahydro-2H-pyran-4-yl)-1H-pyrrolo[3,2-b]pyridine-3-carboxamide 1-[[2-fluoro-4-(1-methylpyrazol-4-yl)phenyl]methyl]-N-[(3S,4S)-4-hydroxyoxan-3-yl]pyrrolo[3,2-b]pyridine-3-carboxamide 1-(2-fluoro-4-(1-methyl-1H-pyrazol-4-yl)benzyl)-N-((3R,4R)-4-hydroxytetrahydro-2H-pyran-3-yl)-1H-pyrrolo[3,2-b]pyridine-3-carboxamide or 1-[[2-fluoro-4-(1-methylpyrazol-4-yl)phenyl]methyl]-N-[(3R,4S) or (3S,4R)-3-hydroxyoxan-4-yl]pyrrolo[3,2-b]pyridine-3-carboxamide.

One embodiment of the present invention are compounds of formula I-A wherein R¹ is pyrazolyl, optionally substituted by lower alkyl and R is lower alkoxy, substituted by hydroxy, lower alkyl substituted by one or two hydroxy, or is (CH₂)ₘ-pyridinyl optionally substituted by hydroxy, lower alkyl or lower alkyl substituted by hydroxy, or is L-phenyl, optionally substituted by hydroxy, lower alkyl or lower alkyl substituted by hydroxy, and L is a bond, —CH(CH₂OH)— or —CH₂CH(OH)—, and n and m are as described above, for example the following compounds rac-1-[2-Fluoro-4-(1-methyl-1H-pyrazol-4-yl)-benzyl]-1H-pyrrolo[3,2-b]pyridine-3-carboxylic acid (2-hydroxy-3-methoxy-propyl)-amide 1-[2-Fluoro-4-(1-methyl-1H-pyrazol-4-yl)-benzyl]-1H-pyrrolo[3,2-b]pyridine-3-carboxylic acid ((S)-2-hydroxy-1-methyl-ethyl)-amide 1-[2-Fluoro-4-(1-methyl-1H-pyrazol-4-yl)-benzyl]-1H-pyrrolo[3,2-b]pyridine-3-carboxylic acid ((R)-2-hydroxy-propyl)-amide 1-[2-Fluoro-4-(1-methyl-1H-pyrazol-4-yl)-benzyl]-1H-pyrrolo[3,2-b]pyridine-3-carboxylic acid ((S)-2-hydroxy-propyl)-amide 1-[2-Fluoro-4-(1-methyl-1H-pyrazol-4-yl)-benzyl]-1H-pyrrolo[3,2-b]pyridine-3-carboxylic acid (2-hydroxy-2-methyl-propyl)-amide 1-[2-Fluoro-4-(1-methyl-1H-pyrazol-4-yl)-benzyl]-1H-pyrrolo[3,2-b]pyridine-3-carboxylic acid ((S)-1-hydroxymethyl-propyl)-amide 1-[2-Fluoro-4-(1-methyl-1H-pyrazol-4-yl)-benzyl]-1H-pyrrolo[3,2-b]pyridine-3-carboxylic acid (1-hydroxymethyl-propyl)-amide 1-[2-Fluoro-4-(1-methyl-1H-pyrazol-4-yl)-benzyl]-1H-pyrrolo[3,2-b]pyridine-3-carboxylic acid (2-hydroxy-butyl)-amide 1-[2-Fluoro-4-(1-methyl-1H-pyrazol-4-yl)-benzyl]-1H-pyrrolo[3,2-b]pyridine-3-carboxylic acid ((R)-2,3-dihydroxy-propyl)-amide 1-[2-Fluoro-4-(1-methyl-1H-pyrazol-4-yl)-benzyl]-1H-pyrrolo[3,2-b]pyridine-3-carboxylic acid ((S)-1-hydroxymethyl-2-methyl-propyl)-amide 1-[2-Fluoro-4-(1-methyl-1H-pyrazol-4-yl)-benzyl]-1H-pyrrolo[3,2-b]pyridine-3-carboxylic acid (1-hydroxymethyl-butyl)-amide 1-[2-Fluoro-4-(1-methyl-1H-pyrazol-4-yl)-benzyl]-1H-pyrrolo[3,2-b]pyridine-3-carboxylic acid ((R)-1-hydroxymethyl-2-methyl-propyl)-amide 1-[2-Fluoro-4-(1-methyl-1H-pyrazol-4-yl)-benzyl]-1H-pyrrolo[3,2-b]pyridine-3-carboxylic acid (1-hydroxymethyl-2-methyl-propyl)-amide 1-[2-Fluoro-4-(1-methyl-1H-pyrazol-4-yl)-benzyl]-1H-pyrrolo[3,2-b]pyridine-3-carboxylic acid ((S)-1-hydroxymethyl-butyl)-amide 1-[2-Fluoro-4-(1-methyl-1H-pyrazol-4-yl)-benzyl]-1H-pyrrolo[3,2-b]pyridine-3-carboxylic acid ((S)-1-hydroxymethyl-3-methyl-butyl)-amide 1-[2-Fluoro-4-(1-methyl-1H-pyrazol-4-yl)-benzyl]-1H-pyrrolo[3,2-b]pyridine-3-carboxylic acid ((1S,2S)-1-hydroxymethyl-2-methyl-butyl)-amide 1-[2-Fluoro-4-(1-methyl-1H-pyrazol-4-yl)-benzyl]-1H-pyrrolo[3,2-b]pyridine-3-carboxylic acid ((S)-1-hydroxymethyl-2,2-dimethyl-propyl)-amide 1-[2-Fluoro-4-(1-methyl-1H-pyrazol-4-yl)-benzyl]-1H-pyrrolo[3,2-b]pyridine-3-carboxylic acid (2-hydroxymethyl-phenyl)-amide 1-[2-Fluoro-4-(1-methyl-1H-pyrazol-4-yl)-benzyl]-1H-pyrrolo[3,2-b]pyridine-3-carboxylic acid (3-hydroxymethyl-pyridin-2-yl)-amide 1-[2-Fluoro-4-(1-methyl-1H-pyrazol-4-yl)-benzyl]-1H-pyrrolo[3,2-b]pyridine-3-carboxylic acid (2-hydroxy-2-phenyl-ethyl)-amide 1-[2-Fluoro-4-(1-methyl-1H-pyrazol-4-yl)-benzyl]-1H-pyrrolo[3,2-b]pyridine-3-carboxylic acid ((S)-2-hydroxy-1-phenyl-ethyl)-amide 1-[2-Fluoro-4-(1-methyl-1H-pyrazol-4-yl)-benzyl]-1H-pyrrolo[3,2-b]pyridine-3-carboxylic acid (2-hydroxymethyl-4-methyl-phenyl)-amide 1-[2-Fluoro-4-(1-methyl-1H-pyrazol-4-yl)-benzyl]-1H-pyrrolo[3,2-b]pyridine-3-carboxylic acid ((S)-2-hydroxy-2-phenyl-ethyl)-amide 1-[2-Fluoro-4-(1-methyl-1H-pyrazol-4-yl)-benzyl]-1H-pyrrolo[3,2-b]pyridine-3-carboxylic acid (3-methyl-pyridin-2-yl)-amide 1-[2-Fluoro-4-(1-methyl-1H-pyrazol-4-yl)-benzyl]-1H-pyrrolo[3,2-b]pyridine-3-carboxylic acid (3-hydroxy-pyridin-2-yl)-amide or 1-(2-fluoro-4-(1-methyl-1H-pyrazol-4-yl)benzyl)-N-((1-hydroxycyclopropyl)methyl)-1H-pyrrolo[3,2-b]pyridine-3-carboxamide.

One embodiment of the present invention are compounds of formula I—B,

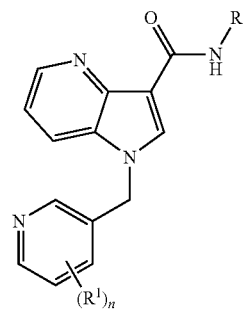

wherein R, $R^1$ and n are as defined above, for example the following compounds 1-((6-chloropyridin-3-yl)methyl)-N-((1S,2S)-2-hydroxycyclohexyl)-1H-pyrrolo[3,2-b]pyridine-3-carboxamide N-((1S,2S)-2-hydroxycyclohexyl)-1-((6-(trifluoromethyl)pyridin-3-yl)methyl)-1H-pyrrolo[3,2-b]pyridine-3-carboxamide N-((1S,2S)-2-hydroxycyclohexyl)-1-((6-(1-methyl-1H-pyrazol-4-yl)pyridin-3-yl)methyl)-1H-pyrrolo[3,2-b]pyridine-3-carboxamide or N-((3RS,4SR)-3-hydroxytetrahydro-2H-pyran-4-yl)-1-((6-(1-methyl-1H-pyrazol-4-yl)pyridin-3-yl)methyl)-1H-pyrrolo[3,2-b]pyridine-3-carboxamide.

One further embodiment of the present invention are compounds of formula I-C

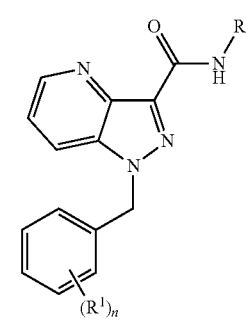

wherein R, $R^1$ and n are as defined above, for example the following compound 1-(2-fluoro-4-(1-methyl-1H-pyrazol-4-yl)benzyl)-N-((1S,2S)-2-hydroxycyclohexyl)-1H-pyrazolo[4,3-b]pyridine-3-carboxamide.

One embodiment of the present invention are compounds of formula I-D

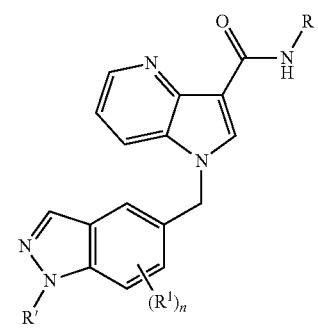

wherein R, $R^1$ and n are as defined above and R' is hydrogen or lower alkyl, for example the following compounds N-((1S,2S)-2-hydroxycyclohexyl)-1-((1-methyl-1H-indazol-5-yl)methyl)-1H-pyrrolo[3,2-b]pyridine-3-carboxamide or N-((1S,2S)-2-hydroxycyclohexyl)-1-(4-(methylcarbamoyl)benzyl)-1H-pyrrolo[3,2-b]pyridine-3-carboxamide.

The present compounds of formula I and their pharmaceutically acceptable salts can be prepared by methods known in the art, for example, by processes described below, which process comprises a) reacting a compound of formula

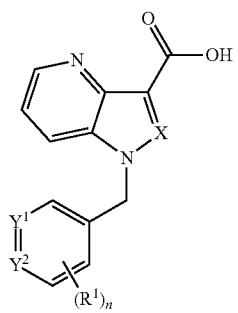

II with a compound of formula

RNH$_2$ in the presence of an activating agent such as BOP (Benzotriazol-1-yloxy)tris(dimethylamino)phosphonium hexafluorophosphate or thionyl chloride to a compound of formula

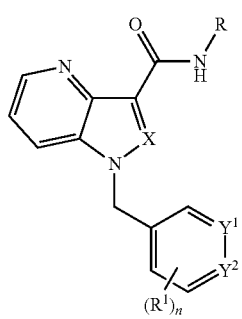

I wherein the substituents are as defined above, or b) reacting a compound of formula

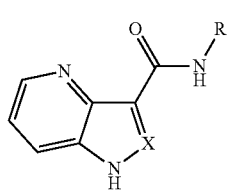

III with a compound of formula

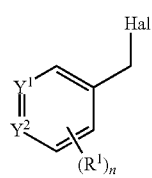

in the presence of base like cesium carbonate to a compound of formula

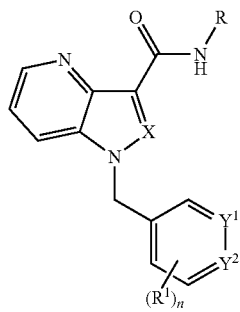

I wherein Hal is halogen and the other substituents are as defined above.

The compounds of formula I may be prepared in accordance with process variant a) or b) and with the following schemes 1-2. The starting material is commercially available or may be prepared in accordance with known methods.

Scheme 1

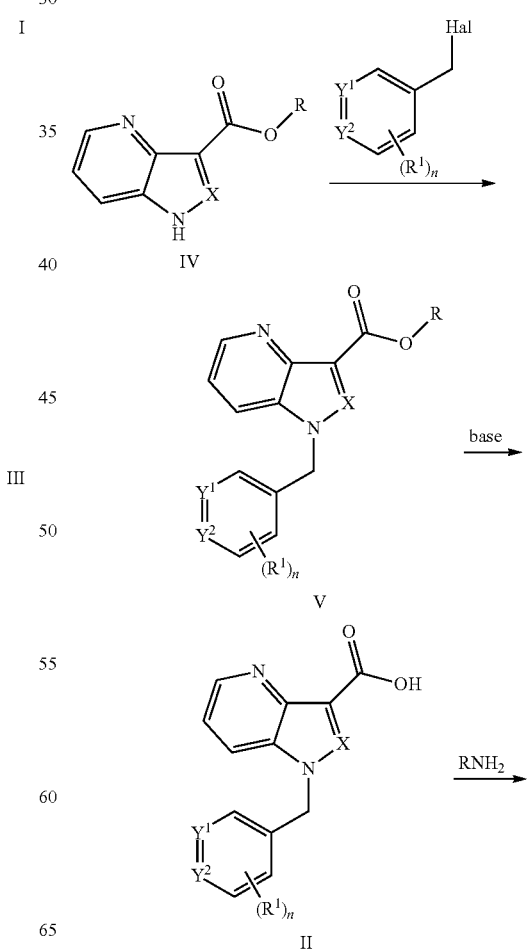

-continued

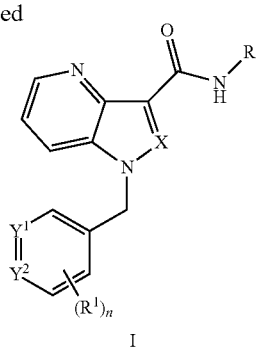

Hal: Cl, Br

Compounds of general formula I can be prepared by reacting ester derivatives of formula IV with an alkylating agent in the presence of a base such as sodium hydride to provide V followed by a saponification of V in the presence of a base such as lithium hydroxide and coupling of the resulting acid II with an amine $RNH_2$.

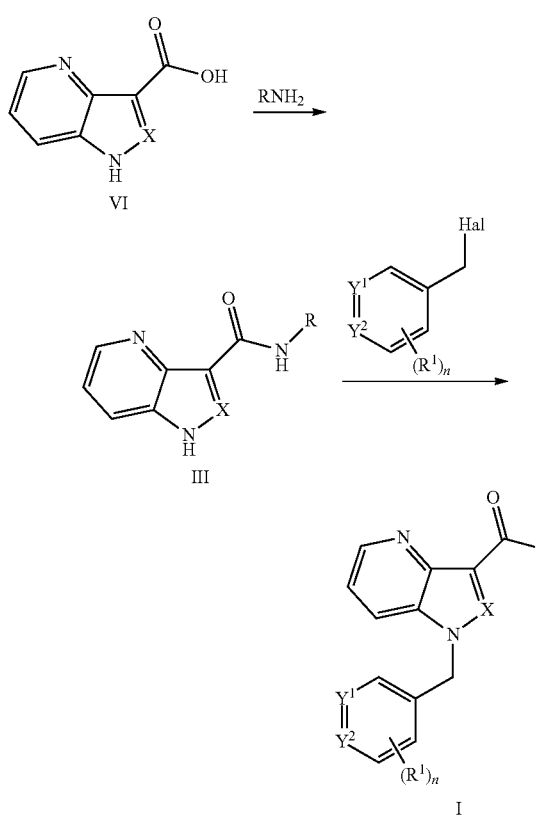

Compounds of general formula I can be prepared by coupling acid derivatives of formula VI with an amine $RNH_2$ to provide amide III followed by reaction of III with an alkylating agent in the presence of a base such as cesium carbonate.

Some substituents $R^1$ may be derived from another precursor substituent at the end of the reaction sequence. For instance, a compound of formula I may be synthesized bearing an ester group as $R^1$, which is converted to a carboxamide substituent by standard procedures.

All reactions are typically performed in a suitable solvent and under an atmosphere of argon or nitrogen.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

M1 PAM Assay

The assay is designed to select compounds that possess modulator activity at the acetylcholine muscarinic receptor expressed in CHO cells by measuring the intracellular calcium with a Fluorometric Imaging Plate Reader System (FLIPR, Molecular Devices). The assay study the effect of several concentrations of test compounds on basal or acetylcholine-stimulated $Ca^{2+}$ levels using FLIPR.

CHO human M1 are plated the day before the experiments at $2\times10^5$ cells/ml in PDL BioCoat 96 well black/clear plate (Becton 35 4640). The cells are grown at 37° C. and 5% $CO_2$ in the following medium: F12 Nut Mix (Gibco 21765), 10% FCS heat inactivated (GIBCO 16000-044), 1% Pen Strep (Gibco, 15140) and 200 µg/ml Geneticin (Gibco 11811). On the day of the experiment, the medium was removed and replaced by 100 µl of dye loading buffer containing Hanks Balanced Salt solution (HBSS, 14065-049, Gibco) with 20 mM HEPES (Gibco 15630-056), 2 mM Probenicid (Sigma P8761), 2 mM Fluo-4AM ester (Molecular Probes F-14202), 10% Pluronic acid Molecular Probes P-3000) pH=7.4 and incubated at 37° C. After 60 minutes extracellular dye was removed and the cells were washed five times with FLIPR buffer containing HBSS (Gibco 14065-049) with 20 mM HEPES (Gibco, 15630-056), 2 mM Probenicid (Sigma P8761) pre-warmed at 37° C. using and Ebml cell washer leaving 100 µl of FLIPR buffer in each well. The cell plate and the diluted compounds (1% DMSO final concentration) are placed on the platform of the FLIPR and the door closed. A signal test to check background fluorescence and basal fluorescence signal is performed. Laser intensity is adjusted if necessary. Two minutes preincubation with the diluted test compounds is provide to determine any agonist activity on the M1 receptor by comparison to 30 nM Acetylcholine control. In order to determine any modulator activity the diluted compounds were added to cells and after two minutes preincubation, the $EC_{20}$ of acetylcholine is added followed by another two minutes preincubation before the measurement of intracellular $Ca^{2+}$ with a FLIPR (Molecular Devices).

| Example | $EC_{50}$ h PAM (uM) | $EC_{50}$ rat PAM (uM) |
|---|---|---|
| 1 | 0.54475 | 1.9451 |
| 2 | 0.00986 | 0.03469 |
| 3 | 0.10142 | 0.1308 |
| 4 | 0.02859 | 0.05865 |
| 5 | 0.48934 | 2.32024 |
| 6 | 0.02528 | 0.07152 |
| 7 | 0.23248 | |
| 8 | 0.24806 | 0.69539 |
| 9 | 0.45868 | |
| 10 | 0.47731 | |
| 11 | 0.31694 | 0.61637 |
| 12 | 0.12923 | 0.24432 |
| 13 | 0.19483 | 0.63159 |
| 14 | 0.10028 | 0.15503 |
| 15 | 0.33332 | |
| 16 | 0.39664 | |
| 17 | 0.06491 | 0.27222 |
| 18 | 0.09596 | 0.19539 |
| 19 | 0.17795 | 0.2852 |
| 20 | 0.1991 | 0.49867 |
| 21 | 0.20108 | |
| 22 | 0.18292 | 0.38092 |
| 23 | 0.20455 | |
| 24 | 0.19322 | 0.26078 |
| 25 | 0.23259 | |
| 26 | 0.14313 | 0.30201 |
| 27 | 0.12561 | 0.35461 |
| 28 | 0.28289 | 0.52126 |
| 29 | 0.29795 | |
| 30 | 0.08241 | 0.2099 |
| 31 | 0.42933 | |
| 32 | 0.08866 | 0.27708 |
| 33 | 0.2818 | |
| 34 | 0.12038 | 0.49442 |
| 35 | 0.32014 | |
| 36 | 0.10876 | 0.31439 |
| 37 | 0.16159 | 0.12313 |
| 38 | 0.36935 | |
| 39 | 0.17685 | 0.26356 |
| 40 | 0.04795 | 0.06322 |
| 41 | 0.03038 | 0.05105 |
| 42 | 0.48692 | |
| 43 | 0.20745 | 0.61132 |
| 44 | 0.12653 | 0.59787 |
| 45 | 0.17733 | 0.54353 |
| 46 | 0.25727 | 0.44363 |
| 47 | 0.16261 | 0.21663 |
| 48 | 1.76833 | 0.42167 |
| 49 | 0.29967 | 0.51192 |
| 50 | 0.31921 | |
| 51 | 0.44295 | |
| 52 | 0.07153 | 0.16258 |
| 53 | 0.3208 | |
| 54 | 0.26413 | |
| 55 | 0.01113 | 0.01387 |
| 56 | 0.03487 | 0.07105 |
| 57 | 0.14336 | 0.13328 |
| 58 | 0.23949 | 0.4535 |
| 59 | 0.01549 | 0.01801 |
| 60 | 0.0382 | 0.126 |
| 61 | 0.0091 | 0.018 |
| 62 | 0.428 | 0.325 |
| 63a | 0.289 | 0.661 |
| 63b | 0.013 | 0.047 |
| 64 | 0.261 | 1.065 |
| 65 | 0.315 | 1.393 |

The 61 compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL PART

Preparation of Intermediates

Example A.1

Preparation of 1-(5-bromo-2-fluorobenzyl)-1H-pyrrolo[3,2-b]pyridine-3-carboxylic acid

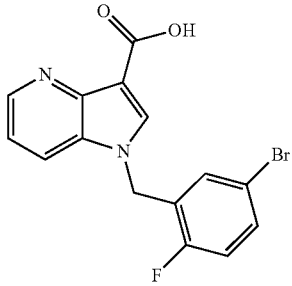 [SMILES: O=C(O)c1cn(Cc2cc(Br)ccc2F)c2cccnc12]

a) Step 1: methyl 1-(5-bromo-2-fluorobenzyl)-1H-pyrrolo[3,2-b]pyridine-3-carboxylate

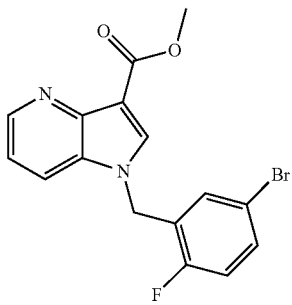 [SMILES: COC(=O)c1cn(Cc2cc(Br)ccc2F)c2cccnc12]

To a solution of methyl 1H-pyrrolo[3,2-b]pyridine-3-carboxylate (200 mg, 1.14 mmol) in DMF (20 ml) under nitrogen at 0° C., was added sodium hydride (90.8 mg, 2.27 mmol). The reaction mixture was vigorously stirred for 30 minutes. 4-bromo-2-(bromomethyl)-1-fluorobenzene (335 mg, 1.25 mmol) was added. The reaction mixture was allowed to warm up to room temperature over 3 hours and was quenched with water (20 ml). The aqueous phase was extracted with ethyl acetate (3×26 ml). The combined organic phases were dried over sodium sulfate and concentrated. The crude yellow oil was purified with flash column chromatography on silica (10 g) eluting with a gradient formed from n-heptane and ethyl acetate (0 to 70%) to provide 39 mg (y: 9.46%) of the title compound as a yellow oil.

b) Step 2: 1-(5-bromo-2-fluorobenzyl)-1H-pyrrolo[3,2-b]pyridine-3-carboxylic acid To a solution of methyl 1-(5-bromo-2-fluorobenzyl)-1H-pyrrolo[3,2-b]pyridine-3-carboxylate (38 mg, 105 μmol) in tetrahydrofuran (380 μl), methanol (190 μl) and water (190 μl) was added lithium hydroxide monohydrate (13.2 mg, 314 mol). The mixture was stirred at room temperature for 24 hours, cooled in an ice-bath and acidified with HCl 5N (80 ul). The suspension was diluted with water. The solid was filtered, washed with water and dried to provide 23 mg (y: 63%) of the title compound as a white solid. MS(m/e): 349.3 (M+H)

Example A.2

Preparation of 1-(2-fluoro-4-(1-methyl-1H-pyrazol-4-yl)benzyl)-1H-pyrrolo[3,2-b]pyridine-3-carboxylic acid

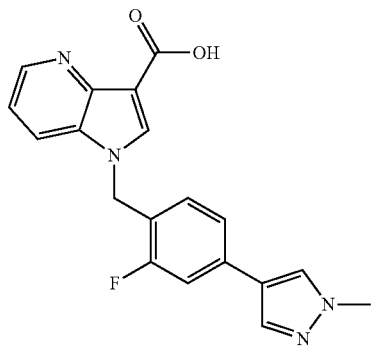 [SMILES: Cn1cc(-c2ccc(Cn3cc(C(=O)O)c4ncccc43)c(F)c2)cn1]

a) Step 1: methyl 1-(4-bromo-2-fluorobenzyl)-1H-pyrrolo[3,2-b]pyridine-3-carboxylate

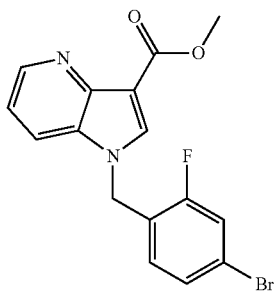 [SMILES: COC(=O)c1cn(Cc2ccc(Br)cc2F)c2cccnc12]

In analogy to the procedure described for the synthesis of example A.1 (step: 1), the title compound was prepared from methyl 1H-pyrrolo[3,2-b]pyridine-3-carboxylate and 4-bromo-1-(bromomethyl)-2-fluorobenzene. MS (m/e): 363 (M+H+).

b) Step 2: methyl 1-(2-fluoro-4-(1-methyl-1H-pyrazol-4-yl)benzyl)-1H-pyrrolo[3,2-b]pyridine-3-carboxylate

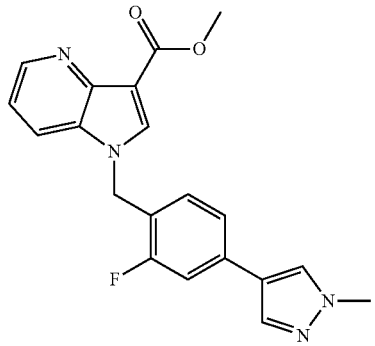 [SMILES: COC(=O)c1cn(Cc2ccc(-c3cnn(C)c3)cc2F)c2cccnc12]

To a solution of tribasic potassium phosphate (29.2 mg, 138 µmol) in water (250 µl) were added methyl 1-(4-bromo-2-fluorobenzyl)-1H-pyrrolo[3,2-b]pyridine-3-carboxylate (50 mg, 138 mol), dioxane (500 µl), 1-methyl-4-(4,4,5,5-tetramethyl-1,3,2-dioxaborolan-2-yl)-1H-pyrazole (35.4 mg, 165 mol), Pd$_2$(dba)$_3$ (1.3 mg, 1.38 mol) and tricyclohexylphosphine (995 µg, 3.44 mol). The mixture was heated at 140° C. under microwave irradiation for 30 minutes. The mixture was diluted with water and ethyl acetate. The organic phase was separated and the aqueous phase was extracted once with ethyl acetate. The combined organic phases were dried over sodium sulfate, filtered and concentrated in vacuo. The crude material was purified on silica eluting with a gradient formed from n-heptane and ethyl acetate (0 to 100%) to provide 37 mg (74%) of the title compound as a white solid. MS (m/e): 365.5 (M+H)$^+$.

c) Step 3: 1-(2-fluoro-4-(1-methyl-1H-pyrazol-4-yl)benzyl)-1H-pyrrolo[3,2-b]pyridine-3-carboxylic acid In analogy to the procedure described for the synthesis of example A.1 (step: 2), the title compound was prepared from methyl 1-(2-fluoro-4-(1-methyl-1H-pyrazol-4-yl)benzyl)-1H-pyrrolo[3,2-b]pyridine-3-carboxylate. MS (m/e): 351.5 (M+H)$^+$.

Example A.3

Preparation of 1-((6-chloropyridin-3-yl)methyl)-1H-pyrrolo[3,2-b]pyridine-3-carboxylic acid hydrochloride

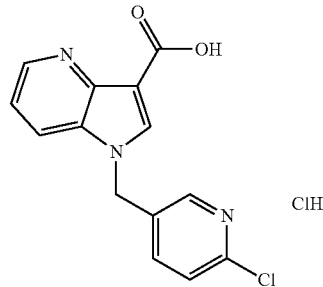 [SMILES: O=C(O)c1cn(Cc2ccc(Cl)nc2)c2cccnc12 ; Cl]

In analogy to the procedure described for the synthesis of example A.1 (steps: 1-2), the title compound was prepared from methyl 1H-pyrrolo[3,2-b]pyridine-3-carboxylate and 5-(bromomethyl)-2-chloropyridine followed by treatment with lithium hydroxide. MS (m/e): 288.4 (M+H)$^+$.

Example A.4

Preparation of 1-(2-fluoro-4-(1-methyl-1H-pyrazol-4-yl)benzyl)-1H-pyrrolo[3,2-b]pyridine-3-carbonyl chloride hydrochloride

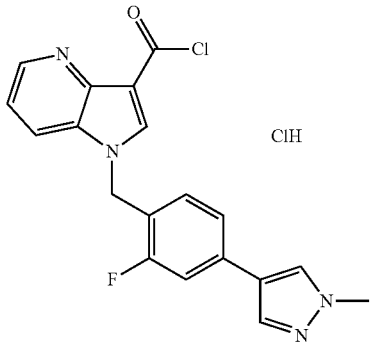 [SMILES: Cn1cc(-c2ccc(Cn3cc(C(=O)Cl)c4ncccc43)c(F)c2)cn1 ; Cl]

To a solution of 1-(2-fluoro-4-(1-methyl-1H-pyrazol-4-yl)benzyl)-1H-pyrrolo[3,2-b]pyridine-3-carboxylic acid (example A2) (500 mg, 1.43 mmol) in dichloroethane (5.00 ml) under nitrogen at room temperature, was added 1 drop of N,N-dimethylformamide, followed by dropwise addition of oxalyl chloride (555 mg, 375 µl, 4.28 mmol). The reaction mixture was stirred in a 50° C. oil bath for 5.5 hours. The mixture was evaporated to dryness to provide 581 mg (100%) of the title compound as an off-white solid.

Example A.5

Preparation of 1-(2-fluoro-4-(1-methyl-1H-pyrazol-4-yl)benzyl)-1H-pyrazolo[4,3-b]pyridine-3-carboxylic acid hydrochloride

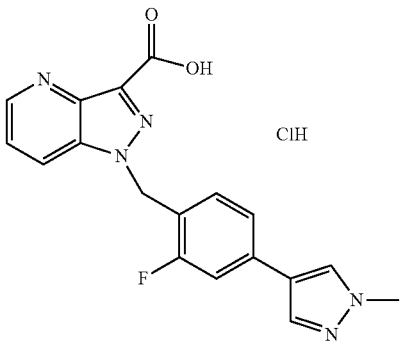 [SMILES: Cn1cc(-c2ccc(Cn3nc(C(=O)O)c4ncccc43)c(F)c2)cn1 ; Cl]

a) Step 1: (2-fluoro-4-(1-methyl-1H-pyrazol-4-yl)phenyl)methanol

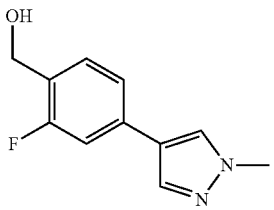

To a mixture of (4-bromo-2-fluorophenyl)methanol (7.3 g, 34.9 mmol), 1-methyl-4-(4,4,5,5-tetramethyl-1,3,2-dioxaborolan-2-yl)-1H-pyrazole (15.1 g, 71.3 mmol) and 1,1'-bis(diphenylphosphino)ferrocene-palladium(II)dichloride dichloromethane complex (1.42 g, 1.74 mmol) in dioxane (104 ml) were added water (83.4 ml) and a 2M sodium carbonate solution (52.3 ml, 105 mmol). The reaction mixture was heated at 80° C., stirred for 2.5 hours, cooled to room temperature and filtered through a glass fiber paper. The solid was washed with a mixture of ethyl acetate and water. The filtrate was extracted with ethyl acetate and the organic phases were washed with water, dried over magnesium sulfate and concentrated in vacuo. The crude material was purified on silica eluting with a gradient formed from n-heptane and ethyl acetate (10 to 80%) to provide 7.07 g (98%) of the title compound as an off-white solid. MS (m/e): 207.5 (M+H)$^+$.

b) Step 2: 4-(4-(chloromethyl)-3-fluorophenyl)-1-methyl-1H-pyrazole

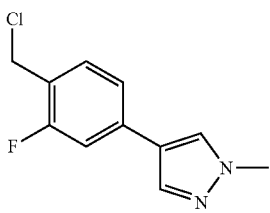

In a 1 L pear-shaped flask, (2-fluoro-4-(1-methyl-1H-pyrazol-4-yl)phenyl)methanol (7.07 g, 34.3 mmol) was dissolved with dichloromethane (389 ml) and thionyl chloride (8.16 g, 5.00 ml, 68.6 mmol) was added. The reaction mixture was heated at 40° C. and stirred for 2.5 h. The crude reaction mixture was concentrated in vacuo and extracted with diethylether. The organic phases were washed twice with a saturated solution of sodium bicarbonate, dried over sodium sulfate and concentrated in vacuo to provide 7.7 g (100%) of the title compound as an off-white solid.

c) Step 3: 1-(2-fluoro-4-(1-methyl-1H-pyrazol-4-yl)benzyl)-1H-pyrazolo[4,3-b]pyridine-3-carboxylic acid hydrochloride In analogy to the procedure described for the synthesis of example A.1 (steps: 1-2), the title compound was prepared from ethyl 1H-pyrazolo[4,3-b]pyridine-3-carboxylate and 4-(4-(chloromethyl)-3-fluorophenyl)-1-methyl-1H-pyrazole followed by treatment with lithium hydroxide. MS (m/e): 352.4 (M+H)$^+$.

Example A.6

Preparation of N-((1S,2S)-2-hydroxycyclohexyl)-1H-pyrrolo[3,2-b]pyridine-3-carboxamide

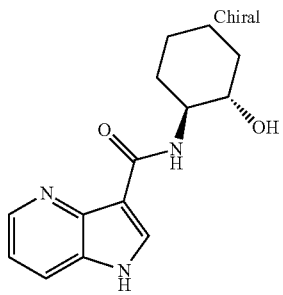 [SMILES: O=C(N[C@H]1CCCC[C@@H]1O)c1c[nH]c2cccnc12]

In a 100 mL pear-shaped flask, 1H-pyrrolo[3,2-b]pyridine-3-carboxylic acid (863 mg, 5.32 mmol), (1S,2S)-(+)-2-aminocyclohexanol hydrochloride (888 mg, 5.85 mmol) and BOP (3.06 g, 6.92 mmol) were combined with dichloromethane (31.9 ml) and triethylamine (2.15 g, 2.97 ml, 21.3 mmol). The reaction mixture was stirred at room temperature overnight, extracted three times with dichloromethane. The organic phases were washed with water and concentrated in vacuo. The crude material was purified on silica eluting with a gradient formed from dichloromethane and methanol (0 to 10%) to provide 0.86 g (62%) of the title compound as a white solid. MS (m/e): 260.5 (M+H)$^+$.

Example A.7

Preparation of N-tetrahydropyran-4-yl-1H-pyrrolo[3,2-b]pyridine-3-carboxamide

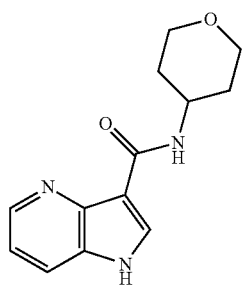 [SMILES: O=C(NC1CCOCC1)c1c[nH]c2cccnc12]

To solution of 1H-pyrrolo[3,2-b]pyridine-3-carboxylic acid (0.4 g, 2.5 mmol), tetrahydro-2H-pyran-4-amine (274 mg, 281 µl, 2.7 mmol) and BOP (1.42 g, 3.2 mmol) in DMF (8 ml) was added TEA (374 mg, 516 µl, 3.7 mmol). The resulting mixture was stirred at 25° C. for 5 hrs. The mixture was quenched with water and extracted with ethyl acetate. The organic layer was washed with water and brine, then it was dried over magnesium sulfate and concentrated to provide the crude product which was used in the next step without further purification. MS (m/e): 281.4 (M+H)⁺.

Example A.8

Preparation of N-[(3RS,4SR)-3-hydroxytetrahydropyran-4-yl]-1H-pyrrolo[3,2-b]pyridine-3-carboxamide

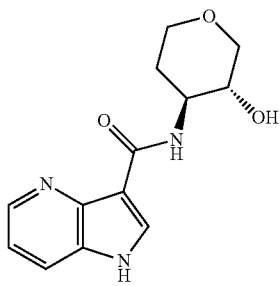 [SMILES: O=C(N[C@H]1CCOC[C@@H]1O)c1c[nH]c2cccnc12]

A solution of 1H-pyrrolo[3,2-b]pyridine-3-carboxylic acid (300 mg, 1.85 mmol), (3RS,4SR)-4-aminotetrahydro-2H-pyran-3-ol hydrochloride (284 mg, 1.85 mmol) and BOP (1.06 g, 2.41 mmol) in dichloromethane (11 ml) was treated with triethylamine (749 mg, 1.03 ml, 7.4 mmol) to give a off-white suspension. The reaction mixture was stirred at r.t. for 4 hrs. The reaction mixture was extracted with dichloromethane and EtOAc. The organic layers were washed water and brine, then concentrated. The crude material was purified by flash chromatography using a $CH_2Cl_2$/MeOH gradient as eluent to provide the title compound (183 mg, 38%) as colorless solid. MS (m/e): 262.1 (M+H)⁺.

DESCRIPTION OF EXAMPLES

Example 1

1-(5-bromo-2-fluorobenzyl)-N-((1S,2S)-2-hydroxycyclohexyl)-1H-pyrrolo[3,2b]pyridine-3-carboxamide and (1S,2S)-2-aminocyclohexanol hydrochloride

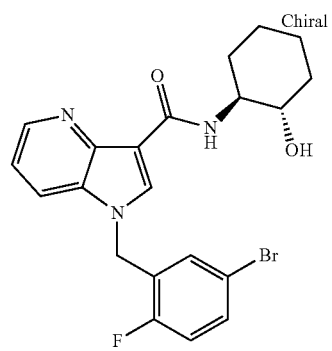 [SMILES: O=C(N[C@H]1CCCC[C@@H]1O)c1cn(Cc2cc(Br)ccc2F)c2cccnc12]

To a suspension of 1-(5-bromo-2-fluorobenzyl)-1H-pyrrolo[3,2-b]pyridine-3-carboxylic acid (example A.1) (21 mg, 60.1 mol) in dichloromethane (400 µl) was added (1S,2S)-2-aminocyclohexanol hydrochloride (10.9 mg, 72.2 mol), (benzotriazol-1-yloxy)tris-(dimethylamino)phosphonium hexafluorophosphate (BOP) (34.6 mg, 78.2 µmol) and triethylamine (24.3 mg, 33.5 µl, 241 µmol). The yellow solution was stirred at room temperature for 4 hours. The solution was diluted with dichloromethane and washed once with water. The aqueous layer was separated and extracted twice with dichloromethane. The combined organic fractions were dried over sodium sulfate, filtered and concentrated in vacuo. The crude material was purified on silica eluting with a gradient formed from n-heptane and ethyl acetate (0 to 100%) to provide 17 mg (63%) of the title compound as a white solid. MS (m/e): 448.4 (M+H)⁺.

In analogy to example 1, examples 2 to 36 of the following table were prepared by coupling an acid derivative with an amine

| Exp No. | Structure | Systematic Name | Starting materials | MW found (MH⁺) |
|---|---|---|---|---|
| 2 | Chiral | 1-(2-fluoro-4-(1-methyl-1H-pyrazol-4-yl)benzyl)-N-((1S,2S)-2-hydroxycyclohexyl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carboxylic acid (example A2) and (1S,2S)-2-aminocyclohexanol hydrochloride | 448.6 |

| Exp No. | Structure | Systematic Name | Starting materials | MW found (MH+) |
|---|---|---|---|---|
| 3 | Chiral 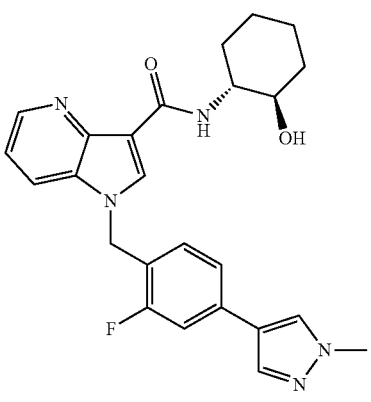 | 1-(2-fluoro-4-(1-methyl-1H-pyrazol-4-yl)benzyl)-N-((1R,2R)-2-hydroxycyclohexyl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carboxylic acid (example A2) and (1R,2R)-2-aminocyclohexanol hydrochloride | 448.6 |
| 4 | Chiral 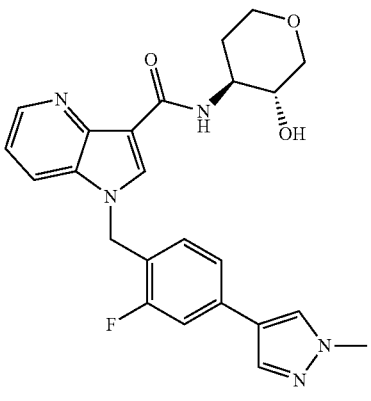 | 1-(2-fluoro-4-(1-methyl-1H-pyrazol-4-yl)benzyl)-N-((3RS,4SR)-3-hydroxytetrahydro-2H-pyran-4-yl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carboxylic acid (example A2) and (3RS,4SR)-4-aminotetrahydro-2H-pyran-3-ol (CAS: 215940-92-4) | 450.5 |
| 5 | Chiral 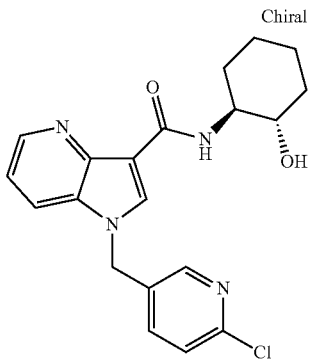 [SMILES: O=C(N[C@H]1CCCC[C@@H]1O)c1cn(Cc2ccc(Cl)nc2)c2cccnc12] | 1-((6-chloropyridin-3-yl)methyl)-N-((1S,2S)-2-hydroxycyclohexyl)-1H-pyrrolo[3,2-b]pyridine-3-carboxamide | 1-((6-chloropyridin-3-yl)methyl)-1H-pyrrolo[3,2-b]pyridine-3-carboxylic acid hydrochloride (example A3) and (1S,2S)-2-aminocyclohexanol hydrochloride | 385.5 |

| Exp No. | Structure | Systematic Name | Starting materials | MW found (MH+) |
|---|---|---|---|---|
| 6 | Chiral | 1-(2-fluoro-4-(1-methyl-1H-pyrazol-4-yl)benzyl)-N-((1S,2S)-2-hydroxycyclohexyl)-1H-pyrazolo[4,3-b]pyridine-3-carboxamide | 1-(2-fluoro-4-(1-methyl-1H-pyrazol-4-yl)benzyl)-1H-pyrazolo[4,3-b]pyridine-3-carboxylic acid hydrochloride (example A5) and (1S,2S)-2-aminocyclohexanol hydrochloride | 449.6 |
| 7 | 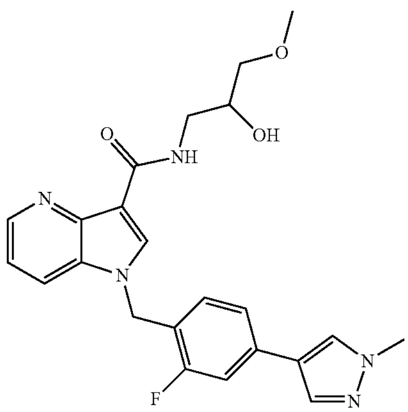 [SMILES: COCC(O)CNC(=O)c1cn(Cc2ccc(-c3cnn(C)c3)cc2F)c2cccnc12] | rac-1-[2-Fluoro-4-(1-methyl-1H-pyrazol-4-yl)-benzyl]-1H-pyrrolo[3,2-b]pyridine-3-carboxylic acid (2-hydroxy-3-methoxy-propyl)-amide | 1-(2-fluoro-4-(1-methyl-1H-pyrazol-4-yl)benzyl)-1H-pyrrolo[3,2-b]pyridine-3-carboxylic acid (example A2) and rac-1-Amino-3-methoxy-propan-ol | 438.0 |
| 8 | Chiral | 1-[2-Fluoro-4-(1-methyl-1H-pyrazol-4-yl)-benzyl]-1H-pyrrolo[3,2-b]pyridine-3-carboxylic acid ((S)-2-hydroxy-1-methyl-ethyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-propan-1-ol | 408.2 |
| 9 | Chiral | 1-[2-Fluoro-4-(1-methyl-1H-pyrazol-4-yl)-benzyl]-1H-pyrrolo[3,2-b]pyridine-3-(carboxylic acid ((R)-2-hydroxy-propyl)-amide | 1-(2-fluoro-4-(1-methyl-1H-pyrazol-4-yl)benzyl)-1H-pyrrolo[3,2-b]pyridine-3-carboxylic acid (example A2) and (R)-1-Amino-propan-2-ol | 408.2 |

| Exp No. | Structure | Systematic Name | Starting materials | MW found (MH+) |
|---|---|---|---|---|
| 10 | Chiral | 1-[2-Fluoro-4-(1-methyl-1H-pyrazol-4-yl)-benzyl]-1H-pyrrolo[3,2-b]pyridine-3-(carboxylic acid ((S)-2-hydroxy-propyl)-amide | 1-(2-fluoro-4-(1-methyl-1H-pyrazol-4-yl)benzyl)-1H-pyrrolo[3,2-b]pyridine-3-carboxylic acid (example A2) and (S)-1-Amino-propan-2-ol | 408.2 |
| 11 | 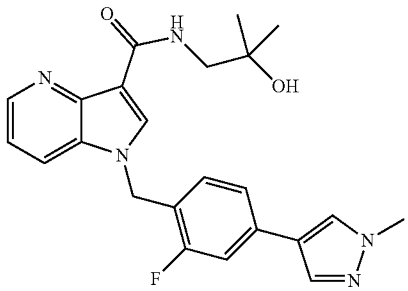 [SMILES: Cn1cc(-c2ccc(Cn3cc(C(=O)NCC(C)(C)O)c4ncccc43)c(F)c2)cn1] | 1-[2-Fluoro-4-(1-methyl-1H-pyrazol-4-yl)-benzyl]-1H-pyrrolo[3,2-b]pyridine-3-carboxylic acid (2-hydroxy-2-methyl-propyl)-amide | 1-(2-fluoro-4-(1-methyl-1H-pyrazol-4-yl)benzyl)-1H-pyrrolo[3,2-b]pyridine-3-carboxylic acid (example A2) and 1-amino-2-methyl-propan-2-ol | 422.0 |
| 12 | Chiral | 1-[2-Fluoro-4-(1-methyl-1H-pyrazol-4-yl)-benzyl]-1H-pyrrolo[3,2-b]pyridine-3-carboxylic acid ((S)-1-hydroxymethyl-propyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-butan-1-ol | 422.0 |
| 13 | 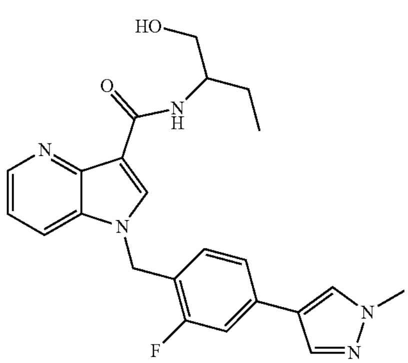 [SMILES: CCC(CO)NC(=O)c1cn(Cc2ccc(-c3cnn(C)c3)cc2F)c2cccnc12] | 1-[2-Fluoro-4-(1-methyl-1H-pyrazol-4-yl)-benzyl]-1H-pyrrolo[3,2-b]pyridine-3-carboxylic acid (1-hydroxymethyl-propyl)-amide | 1-(2-fluoro-4-(1-methyl-1H-pyrazol-4-yl)benzyl)-1H-pyrrolo[3,2-b]pyridine-3-carboxylic acid (example A2) and 2-Amino-butan-1-ol | 422.0 |

| Exp No. | Structure | Systematic Name | Starting materials | MW found (MH+) |
|---|---|---|---|---|
| 14 | 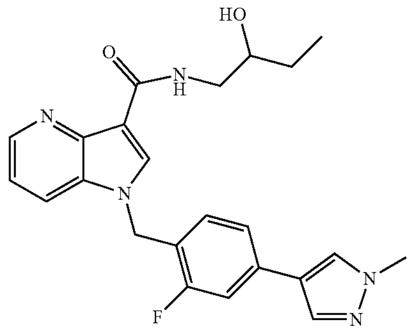 [SMILES: CCC(O)CNC(=O)c1cn(Cc2ccc(-c3cnn(C)c3)cc2F)c2cccnc12] | 1-[2-Fluoro-4-(1-methyl-1H-pyrazol-4-yl)-benzyl]-1H-pyrrolo[3,2-b]pyridine-3-carboxylic acid (2-hydroxy-butyl)-amide | 1-(2-fluoro-4-(1-methyl-1H-pyrazol-4-yl)benzyl)-1H-pyrrolo[3,2-b]pyridine-3-carboxylic acid (example A2) and 1-Amino-butan-2-ol | 422.0 |
| 15 | Chiral | 1-[2-Fluoro-4-(1-methyl-1H-pyrazol-4-yl)-benzyl]-1H-pyrrolo[3,2-b]pyridine-3-carboxylic acid ((R)-2,3-dihydroxy-propyl)-amide | 1-(2-fluoro-4-(1-methyl-1H-pyrazol-4-yl)benzyl)-1H-pyrrolo[3,2-b]pyridine-3-carboxylic acid (example A2) and (R)-3-Amino-propane-1,2-diol | 424.2 |
| 16 | Chiral | 1-[2-Fluoro-4-(1-methyl-1H-pyrazol-4-yl)-benzyl]-1H-pyrrolo[3,2-b]pyridine-3-carboxylic acid ((1R,2R)-2-hydroxy-cyclopentyl)-amide | 1-(2-fluoro-4-(1-methyl-1H-pyrazol-4-yl)benzyl)-1H-pyrrolo[3,2-b]pyridine-3-carboxylic acid (example A2) and (1R,2R)-2-Amino-cyclopentanol | 434.0 |
| 17 | Chiral | 1-[2-Fluoro-4-(1-methyl-1H-pyrazol-4-yl)-benzyl]-1H-pyrrolo[3,2-b]pyridine-3-carboxylic acid ((1S,2S)-2-hydroxy-cyclopentyl)-amide | 1-(2-fluoro-4-(1-methyl-1H-pyrazol-4-yl)benzyl)-1H-pyrrolo[3,2-b]pyridine-3-carboxylic acid (example A2) and (1S,2S)-2-Amino-cyclopentanol | 434.2 |

| Exp No. | Structure | Systematic Name | Starting materials | MW found (MH+) |
|---|---|---|---|---|
| 18 | Chiral | 1-[2-Fluoro-4-(1-methyl-1H-pyrazol-4-yl)-benzyl]-1H-pyrrolo[3,2-b]pyridine-3-carboxylic acid ((1S,2R)-2-hydroxy-cyclopentyl)-amide | 1-(2-fluoro-4-(1-methyl-1H-pyrazol-4-yl)benzyl)-1H-pyrrolo[3,2-b]pyridine-3-carboxylic acid (example A2) and (1S,2R)-2-Amino-cyclopentanol | 434.2 |
| 19 | Chiral | 1-[2-Fluoro-4-(1-methyl-1H-pyrazol-4-yl)-benzyl]-1H-pyrrolo[3,2-b]pyridine-3-carboxylic acid ((S)-1-hydroxymethyl-2-methyl-propyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-3-methyl-butan-1-ol | 436.2 |
| 20 | 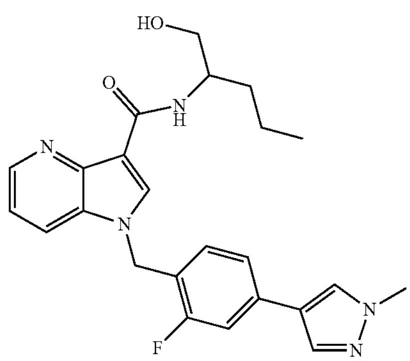 [SMILES: CCCC(CO)NC(=O)c1cn(Cc2ccc(-c3cnn(C)c3)cc2F)c2cccnc12] | 1-[2-Fluoro-4-(1-methyl-1H-pyrazol-4-yl)-benzyl]-1H-pyrrolo[3,2-b]pyridine-3-carboxylic acid (1-hydroxymethyl-butyl)-amide | 1-(2-fluoro-4-(1-methyl-1H-pyrazol-4-yl)benzyl)-1H-pyrrolo[3,2-b]pyridine-3-carboxylic acid (example A2) and 2-Amino-pentan-1-ol | 436.2 |
| 21 | Chiral | 1-[2-Fluoro-4-(1-methyl-1H-pyrazol-4-yl)-benzyl]-1H-pyrrolo[3,2-b]pyridine-3-carboxylic acid ((R)-1-hydroxymethyl-2-methyl-propyl)-amide | 1-(2-fluoro-4-(1-methyl-1H-pyrazol-4-yl)benzyl)-1H-pyrrolo[3,2-b]pyridine-3-carboxylic acid (example A2) and (R)-2-Amino-3-methyl-butan-1-ol | 436.2 |

-continued

| Exp No. | Structure | Systematic Name | Starting materials | MW found (MH+) |
|---|---|---|---|---|
| 22 | 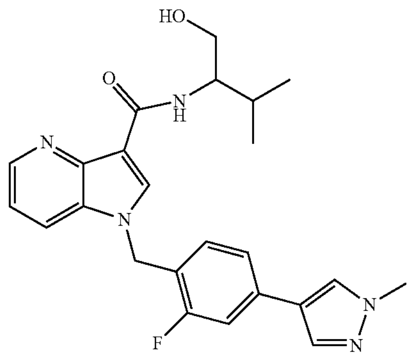 [SMILES: CC(C)C(CO)NC(=O)c1cn(Cc2ccc(-c3cnn(C)c3)cc2F)c2cccnc12] | 1-[2-Fluoro-4-(1-methyl-1H-pyrazol-4-yl)-benzyl]-1H-pyrrolo[3,2-b]pyridine-3-carboxylic acid (1-hydroxymethyl-2-methyl-propyl)-amide | 1-(2-fluoro-4-(1-methyl-1H-pyrazol-4-yl)benzyl)-1H-pyrrolo[3,2-b]pyridine-3-carboxylic acid (example A2) and 2-Amino-3-methyl-butan-1-ol | 436.2 |
| 23 | Chiral | 1-[2-Fluoro-4-(1-methyl-1H-pyrazol-4-yl)-benzyl]-1H-pyrrolo[3,2-b]pyridine-3-carboxylic acid ((S)-1-hydroxymethyl-butyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-pentan-1-ol | 436.2 |
| 24 | 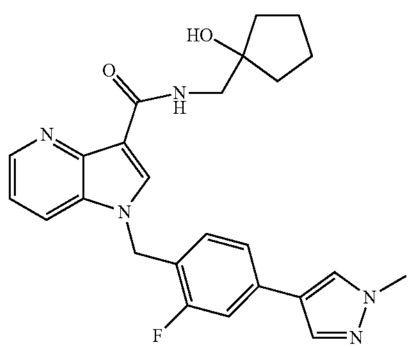 [SMILES: Cn1cc(-c2ccc(Cn3cc(C(=O)NCC4(O)CCCC4)c4ncccc43)c(F)c2)cn1] | 1-[2-Fluoro-4-(1-methyl-1H-pyrazol-4-yl)-benzyl]-1H-pyrrolo[3,2-b]pyridine-3-carboxylic acid (1-hydroxy-cyclopentylmethyl)-amide | 1-(2-fluoro-4-(1-methyl-1H-pyrazol-4-yl)benzyl)-1H-pyrrolo[3,2-b]pyridine-3-carboxylic acid (example A2) and 1-Aminomethyl-cyclopentanol | 448.0 |
| 25 | Chiral | 1-[2-Fluoro-4-(1-methyl-1H-pyrazol-4-yl)-benzyl]-1H-pyrrolo[3,2-b]pyridine-3-carboxylic acid ((S)-1-hydroxymethyl-3-methyl-butyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-4-methyl-pentan-ol | 450.0 |

| Exp No. | Structure | Systematic Name | Starting materials | MW found (MH+) |
|---|---|---|---|---|
| 26 | Chiral | 1-[2-Fluoro-4-(1-methyl-1H-pyrazol-4-yl)-benzyl]-1H-pyrrolo[3,2-b]pyridine-3-carboxylic acid ((1S,2S)-1-hydroxymethyl-2-methyl-butyl)-amide | 1-(2-fluoro-4-(1-methyl-1H-pyrazol-4-yl)benzyl)-1H-pyrrolo[3,2-b]pyridine-3-carboxylic acid (example A2) and (2S,3S)-2-Amino-3-methyl-pentan-1-ol | 450.0 |
| 27 | Chiral | 1-[2-Fluoro-4-(1-methyl-1H-pyrazol-4-yl)-benzyl]-1H-pyrrolo[3,2-b]pyridine-3-carboxylic acid ((S)-1-hydroxymethyl-2,2-dimethyl-propyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-3,3-dimethyl-butan-1-ol | 450.0 |
| 28 | 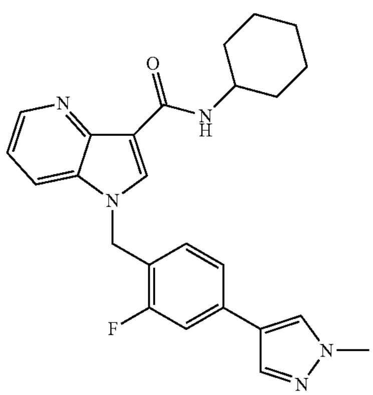 [SMILES: Cn1cc(-c2ccc(Cn3cc(C(=O)NC4CCCCC4)c4ncccc43)c(F)c2)cn1] | N-cyclohexyl-1-(2-fluoro-4-(1-methyl-1H-pyrazol-4-yl)benzyl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carboxylic acid (example A2) and cyclohexylamine | 432.5 |
| 29 | 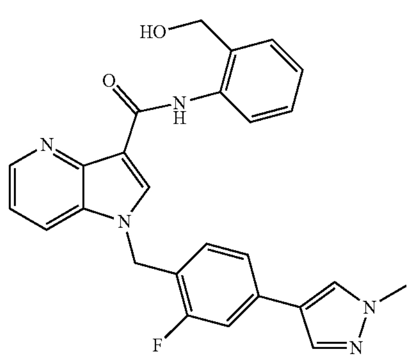 [SMILES: Cn1cc(-c2ccc(Cn3cc(C(=O)Nc4ccccc4CO)c4ncccc43)c(F)c2)cn1] | 1-[2-Fluoro-4-(1-methyl-1H-pyrazol-4-yl)-benzyl]-1H-pyrrolo[3,2-b]pyridine-3-carboxylic acid (2-hydroxymethyl-phenyl)-amide | 1-(2-fluoro-4-(1-methyl-1H-pyrazol-4-yl)benzyl)-1H-pyrrolo[3,2-b]pyridine-3-carboxylic acid (example A2) and (2-Amino-phenyl)-methanol | 456.0 |

-continued

| Exp No. | Structure | Systematic Name | Starting materials | MW found (MH+) |
|---|---|---|---|---|
| 30 | 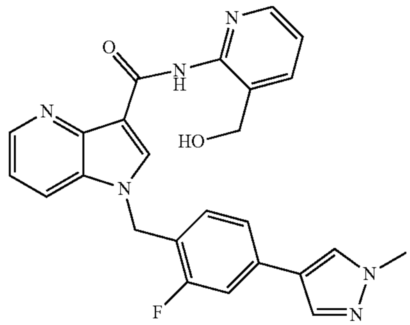 [SMILES: Cn1cc(-c2ccc(Cn3cc(C(=O)Nc4ncccc4CO)c4ncccc43)c(F)c2)cn1] | 1-[2-Fluoro-4-(1-methyl-1H-pyrazol-4-yl)-benzyl]-1H-pyrrolo[3,2-b]pyridine-3-carboxylic acid (3-hydroxymethyl-pyridin-2-yl)-amide | 1-(2-fluoro-4-(1-methyl-1H-pyrazol-4-yl)benzyl)-1H-pyrrolo[3,2-b]pyridine-3-carboxylic acid (example A2) and (2-Amino-pyridin-3-yl)-methanol | 457.2 |
| 31 | 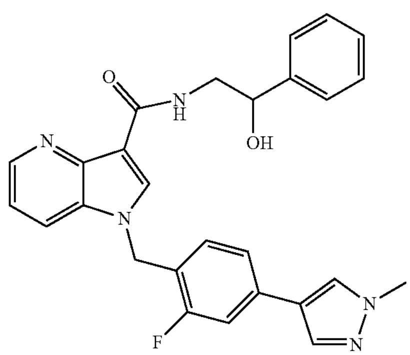 [SMILES: Cn1cc(-c2ccc(Cn3cc(C(=O)NCC(O)c4ccccc4)c4ncccc43)c(F)c2)cn1] | 1-[2-Fluoro-4-(1-methyl-1H-pyrazol-4-yl)-benzyl]-1H-pyrrolo[3,2-b]pyridine-3-carboxylic acid (2-hydroxy-2-phenyl-ethyl)-amide | 1-(2-fluoro-4-(1-methyl-1H-pyrazol-4-yl)benzyl)-1H-pyrrolo[3,2-b]pyridine-3-carboxylic acid (example A2) and 2-Amino-1-phenyl-ethanol | 470.4 |
| 32 | Chiral | 1-[2-Fluoro-4-(1-methyl-1H-pyrazol-4-yl)-benzyl]-1H-pyrrolo[3,2-b]pyridine-3-carboxylic acid ((S)-2-hydroxy-1-phenyl-ethyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-2-phenyl-ethanol | 470.2 |

-continued

| Exp No. | Structure | Systematic Name | Starting materials | MW found (MH+) |
|---|---|---|---|---|
| 33 | 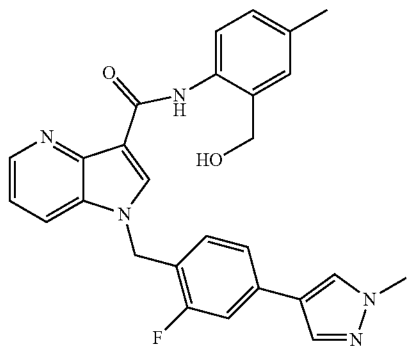 [SMILES: Cc1ccc(NC(=O)c2cn(Cc3ccc(-c4cnn(C)c4)cc3F)c3cccnc23)c(CO)c1] | 1-[2-Fluoro-4-(1-methyl-1H-pyrazol-4-yl)-benzyl]-1H-pyrrolo[3,2-b]pyridine-3-carboxylic acid (2-hydroxymethyl-4-methyl-phenyl)-amide | 1-(2-fluoro-4-(1-methyl-1H-pyrazol-4-yl)benzyl)-1H-pyrrolo[3,2-b]pyridine-3-carboxylic acid (example A2) and (2-Amino-5-methyl-phenyl)-methanol | 470.2 |
| 34 | Chiral | 1-[2-Fluoro-4-(1-methyl-1H-pyrazol-4-yl)-benzyl]-1H-pyrrolo[3,2-b]pyridine-3-carboxylic acid ((S)-2-hydroxy-2-phenyl-ethyl)-amide | 1-(2-fluoro-4-(1-methyl-1H-pyrazol-4-yl)benzyl)-1H-pyrrolo[3,2-b]pyridine-3-carboxylic acid (example A2) and (S)-2-Amino-1-phenyl-ethanol | 470.0 |
| 35 | 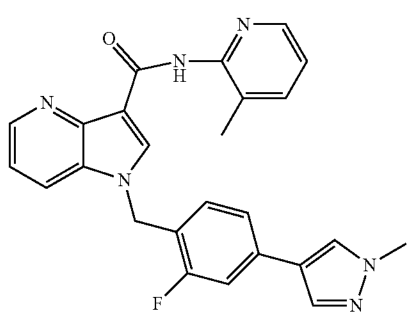 [SMILES: Cc1cccnc1NC(=O)c1cn(Cc2ccc(-c3cnn(C)c3)cc2F)c2cccnc12] | 1-[2-Fluoro-4-(1-methyl-1H-pyrazol-4-yl)-benzyl]-1H-pyrrolo[3,2-b]pyridine-3-carboxylic acid (3-methyl-pyridin-2-yl)-amide | 1-(2-fluoro-4-(1-methyl-1H-pyrazol-4-yl)benzyl)-1H-pyrrolo[3,2-b]pyridine-3-carboxylic acid (example A2) and 3-Methyl-pyridin-2-ylamide | 441.0 |
| 36 | 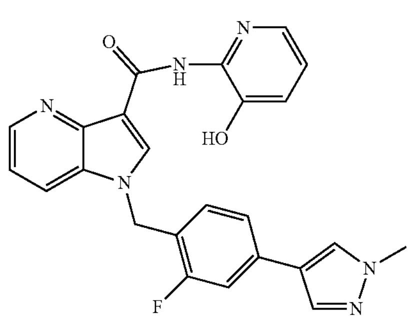 [SMILES: Cn1cc(-c2ccc(Cn3cc(C(=O)Nc4ncccc4O)c4ncccc43)c(F)c2)cn1] | 1-[2-Fluoro-4-(1-methyl-1H-pyrazol-4-yl)-benzyl]-1H-pyrrolo[3,2-b]pyridine-3-carboxylic acid (3-hydroxy-pyridin-2-yl)-amide | 1-(2-fluoro-4-(1-methyl-1H-pyrazol-4-yl)benzyl)-1H-pyrrolo[3,2-b]pyridine-3-carboxylic acid (example A2) and 2-Amino-pyridin-3-ol | 443.2 |

Example 37

(1-(2-fluoro-4-(1-methyl-1H-pyrazol-4-yl)benzyl)-N-((1SR,2RS)-2 hydroxycyclohexyl)-1H-pyrrolo[3,2-b]pyridine-3-carboxamide

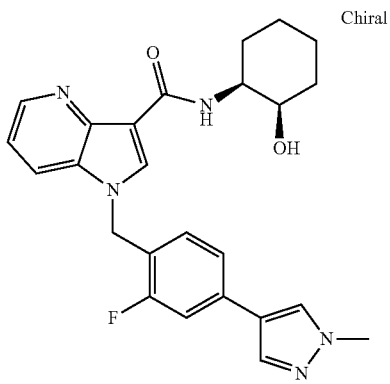 [SMILES: Cn1cc(-c2ccc(Cn3cc(C(=O)N[C@H]4CCCC[C@H]4O)c4ncccc43)c(F)c2)cn1]

To a suspension of 1-(2-fluoro-4-(1-methyl-1H-pyrazol-4-yl)benzyl)-1H-pyrrolo[3,2-b]pyridine-3-carbonyl chloride hydrochloride (Example A4) (100 mg, 247 µmol) in N,N-dimethylformamide (1.00 ml) under nitrogen at room temperature, was added triethylamine (99.9 mg, 137 µl, 987 µmol). After 5 minutes, cis-2-aminocyclohexanol hydrochloride (41.6 mg, 271 µmol) was added and the reaction mixture was stirred at room temperature for 30 minutes. The mixture was purified by preparative HPLC. The pure product was crystallized in diethyl ether and dried to provide 49 mg (y: 44.4%) of the title compound as a white solid. MS (m/e): 448.5 (M+H)$^+$.

In analogy to Example 37, compounds 38 to 42 of the following table were prepared from 1-(2-fluoro-4-(1-methyl-H-pyrazol-4-yl)benzyl)-1H-pyrrolo[3,2-b]pyridine-3-carbonyl chloride hydrochloride (example A4) and an amine derivative:

| Expl. No. | Structure | Systematic Name | Starting materials | MW found (MH$^+$) |
|---|---|---|---|---|
| 38 | 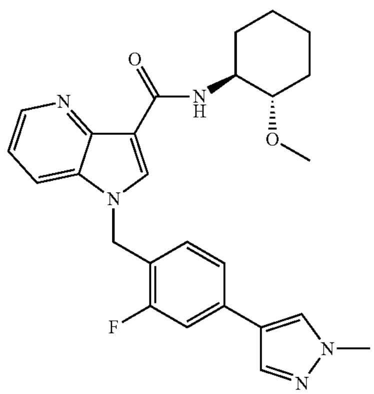 | 1-[2-Fluoro-4-(1-methyl-1H-pyrazol-4-yl)-benzyl]-1H-pyrrolo[3,2-b]pyridine-3-carboxylic acid ((1S,2S)-2-methoxy-cyclohexyl)-amide | 1-(2-fluoro-4-(1-methyl-1H-pyrazol-4-yl)benzyl)-1H-pyrrolo[3,2-b]pyridine-3-carbonyl chloride hydrochloride (example A4) and (1S,2S)-2-methoxycyclohexanamine hydrochloride | 462.5 |
| 39 | 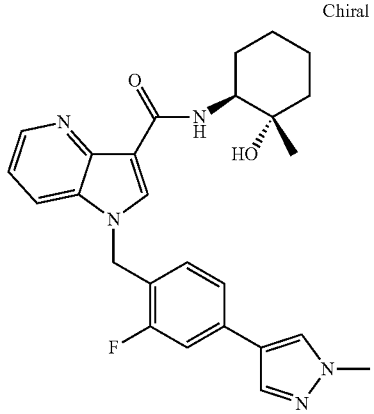 [SMILES: Cn1cc(-c2ccc(Cn3cc(C(=O)N[C@H]4CCCC[C@]4(C)O)c4ncccc43)c(F)c2)cn1] | 1-(2-fluoro-4-(1-methyl-1H-pyrazol-4-yl)benzyl)-N-((1SR,2SR)-2-hydroxy-2-methylcyclohexyl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carbonyl chloride hydrochloride (example A4) and (1RS,2RS)-2-amino-1-methylcyclohexanol hydrochloride (CAS: 837377-18-1) | 462.4 |

-continued

| Expl. No. | Structure | Systematic Name | Starting materials | MW found (MH+) |
|---|---|---|---|---|
| 40 | Chiral | 1-(2-fluoro-4-(1-methyl-1H-pyrazol-4-yl)benzyl)-N-((1SR,2RS)-2-hydroxy-2-methylcyclohexyl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carbonyl chloride hydrochloride (example A4) and (1RS,2SR)-2-amino-1-methylcyclohexanol hydrochloride (CAS: 837377-17-0) | 462.5 |
| 41 | Chiral | 1-[[2-fluoro-4-(1-methylpyrazol-4-yl)phenyl]methyl]-N-[(3S,4S)-4-hydroxyoxan-3-yl]pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carbonyl chloride hydrochloride (example A4) and (3S,4S)-3-aminotetrahydro-2H-pyran-4-ol | 450.5 |
| 42 | Chiral | 1-(2-fluoro-4-(1-methyl-1H-pyrazol-4-yl)benzyl)-N-((3R,4R)-4-hydroxytetrahydro-2H-pyran-3-yl)-1H-pyrrolo[3,2-b]pyridine-3-carboxamide | 1-(2-fluoro-4-(1-methyl-1H-pyrazol-4-yl)benzyl)-1H-pyrrolo[3,2-b]pyridine-3-carbonyl chloride hydrochloride (example A4) and (3R,4R)-3-aminotetrahydro-2H-pyran-4-ol | 450.4 |

Example 43

N-((1S,2S)-2-hydroxycyclohexyl)-1-(4-methylbenzyl)-1H-pyrrolo[3,2-b]pyridine-3-carboxamide

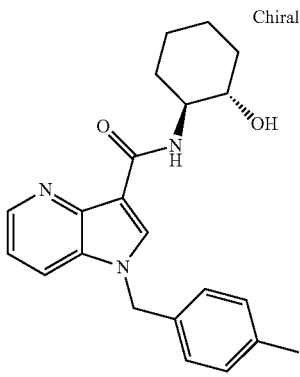 [SMILES: Cc1ccc(Cn2cc(C(=O)N[C@H]3CCCC[C@@H]3O)c3ncccc32)cc1]

In a sealed tube, N-((1S,2S)-2-hydroxycyclohexyl)-1H-pyrrolo[3,2-b]pyridine-3-carboxamide (example A6) (30 mg, 116 µmol), 1-(bromomethyl)-4-methylbenzene (21.8 mg, 116 µmol) and cesium carbonate (37.7 mg, 116 µmol) were combined with DMA (700 µl). The reaction mixture was stirred at room temperature overnight, quenched with water, extracted with ethyl acetate. The combined organic phases were washed with water were washed, dried over magnesium sulfate and concentrated in vacuo. HPLC purification provided 24 mg (57%) of the title compound as a light yellow solid. MS(m/e): 364.5 (M+H)$^+$.

In analogy to Example 43, compounds 44 to 55 of the following table were prepared by reaction of N-((1S,2S)-2-hydroxycyclohexyl)-1H-pyrrolo[3,2-b]pyridine-3-carboxamide (example A6) with an alkylating agent

| Expl. No. | Structure | Systematic Name | Starting materials | MW found (MH$^+$) |
|---|---|---|---|---|
| 44 | Chiral structure | 1-(3-fluoro-4-methoxybenzyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(bromomethyl)-2-fluoro-1-methoxybenzene | 398.5 |
| 45 | Chiral structure | 1-(4-cyanobenzyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(bromomethyl)benzonitrile | 375.5 |

| Expl. No. | Structure | | Systematic Name | Starting materials | MW found (MH+) |
|---|---|---|---|---|---|
| 46 | 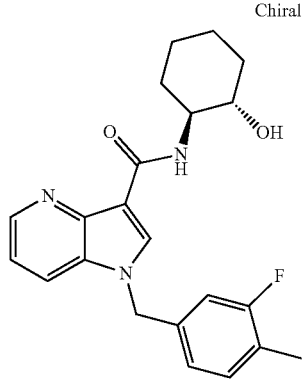 [SMILES: Cc1ccc(Cn2cc(C(=O)N[C@H]3CCCC[C@@H]3O)c3ncccc32)cc1F] | Chiral | 1-(3-fluoro-4-methylbenzyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(chloromethyl)-2-fluoro-1-methylbenzene | 382.5 |
| 47 | 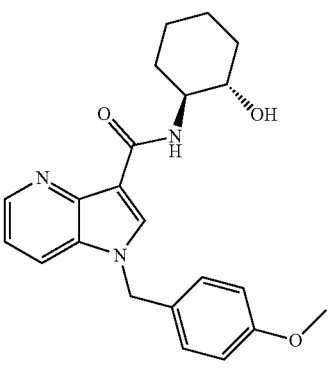 | Chiral | N-((1S,2S)-2-hydroxycyclohexyl)-1-(4-methoxybenzyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 1-(chloromethyl)-4-methoxybenzene | 380.5 |
| 48 | 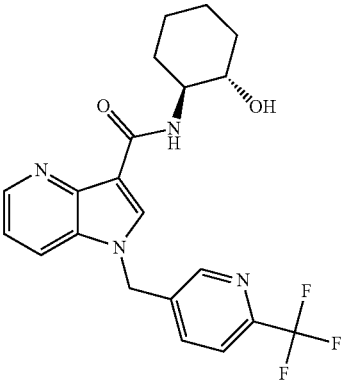 | Chiral | N-((1S,2S)-2-hydroxycyclohexyl)-1-((6-(trifluoromethyl)pyridin-3-yl)methyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 5-(chloromethyl)-2-(trifluoromethyl)pyridine | 419.5 |

-continued

| Expl. No. | Structure | Systematic Name | Starting materials | MW found (MH+) |
|---|---|---|---|---|
| 49 | Chiral | 1-(biphenyl-4-ylmethyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(chloromethyl) biphenyl | 426.5 |
| 50 | Chiral | 1-(4-bromobenzyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 1-bromo-4-(bromomethyl)benzene | 428.5 |
| 51 | Chiral | N-((1S,2S)-2-hydroxycyclohexyl)-1-(3-(1-methyl-1H-pyrazol-4-yl)benzyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(3-(chloromethyl) phenyl)-1-methyl-1H-pyrazole | 430.7 |

-continued

| Expl. No. | Structure | Systematic Name | Starting materials | MW found (MH+) |
|---|---|---|---|---|
| 52 | 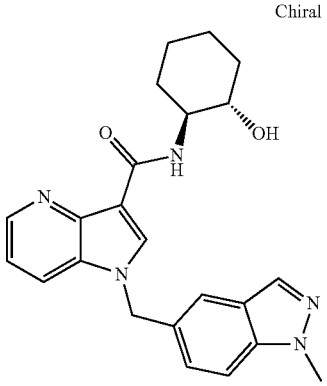 [SMILES: Cn1ncc2cc(Cn3cc(C(=O)N[C@H]4CCCC[C@@H]4O)c4ncccc43)ccc21] Chiral | N-((1S,2S)-2-hydroxycyclohexyl)-1-((1-methyl-1H-indazol-5-yl)methyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 5-(bromomethyl)-1-methyl-1H-indazole | 404.5 |
| 53 | 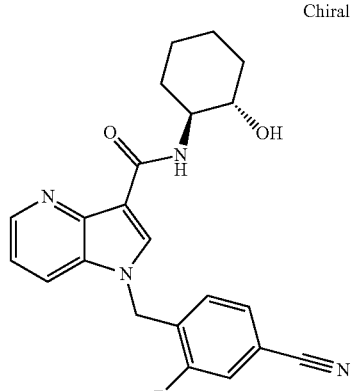 Chiral | 1-(4-cyano-2-fluorobenzyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(bromomethyl)-3-fluorobenzonitrile | 393.5 |
| 54 | 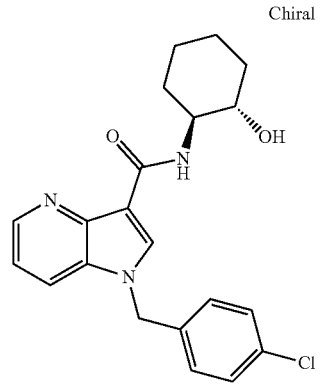 [SMILES: O=C(N[C@H]1CCCC[C@@H]1O)c1cn(Cc2ccc(Cl)cc2)c2cccnc12] Chiral | 1-(4-chlorobenzyl)-N-((1S,2S)-2-hydroxycyclohexyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 1-chloro-4-(chloromethyl)benzene | 384.4 |

| Expl. No. | Structure | Systematic Name | Starting materials | MW found (MH+) |
|---|---|---|---|---|
| 55 | Chiral | N-((1S,2S)-2-hydroxycyclohexyl)-1-(4-(1-methyl-1H-pyrazol-4-yl)benzyl)-1H-pyrrolo[3,2-b]pyridine-3-carboxamide | N-((1S,2S)-2-hydroxycyclohexyl)-1H-pyrrolo[3,2-b]pyridine-3-carboxamide (example A6) and 4-(4-(chloromethyl)phenyl)-1-methyl-1H-pyrazole | 430.7 |

Example 56

N-((1S,2S)-2-hydroxycyclohexyl)-1-((6-(1-methyl-1H-pyrazol-4-yl)pyridin-3-yl)methyl)-1H-pyrrolo[3,2-b]pyridine-3-carboxamide

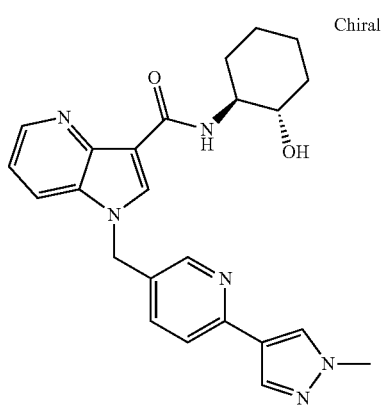 [SMILES: Cn1cc(-c2ccc(Cn3cc(C(=O)N[C@H]4CCCC[C@@H]4O)c4ncccc43)cn2)cn1]

In analogy to the procedure described for the synthesis of example A.2 (step: 2), the title compound was prepared from 1-((6-chloropyridin-3-yl)methyl)-N-((1S,2S)-2-hydroxycyclohexyl)-1H-pyrrolo[3,2-b]pyridine-3-carboxamide (example 5) with 1-methyl-4-(4,4,5,5-tetramethyl-1,3,2-dioxaborolan-2-yl)-1H-pyrazole. MS (m/e): 431.6 (M+H)+.

Example 57

Preparation of N-((3RS,4SR)-3-hydroxytetrahydro-2H-pyran-4-yl)-1-((6-(1-methyl-1H-pyrazol-4-yl)pyridin-3-yl)methyl)-1H-pyrrolo[3,2-b]pyridine-3-carboxamide

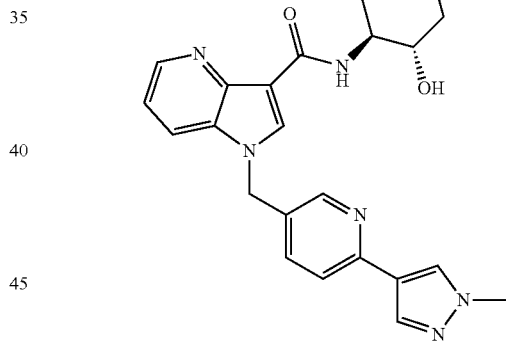

a) Step 1: 1-((6-chloropyridin-3-yl)methyl)-N-((3RS,4SR)-3-hydroxytetrahydro-2H-pyran-4-yl)-1H-pyrrolo[3,2-b]pyridine-3-carboxamide

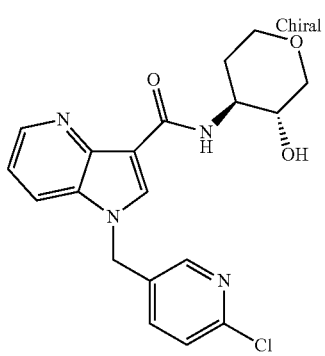 [SMILES: O=C(N[C@H]1CCOC[C@@H]1O)c1cn(Cc2ccc(Cl)nc2)c2cccnc12]

In analogy to the procedure described for the synthesis of example 1, the title compound was prepared from 1-((6-chloropyridin-3-yl)methyl)-1H-pyrrolo[3,2-b]pyridine-3-carboxylic acid hydrochloride (example A3) and (3RS,4SR)-4-aminotetrahydro-2H-pyran-3-ol (CAS: 215940-92-4). MS (m/e): 387.5 (M+H)+.

a) Step 2: N-((3RS,4SR)-3-hydroxytetrahydro-2H-pyran-4-yl)-1-((6-(1-methyl-1H-pyrazol-4-yl)pyridin-3-yl)methyl)-1H-pyrrolo[3,2-b]pyridine-3-carboxamide In analogy to the procedure described for the synthesis of example A.2 (steps: 2), the title compound was prepared from 1-((6-chloropyridin-3-yl)methyl)-N-((3RS,4SR)-3-hydroxytetrahydro-2H-pyran-4-yl)-1H-pyrrolo[3,2-b]pyridine-3-carboxamide with 1-methyl-4-(4,4,5,5-tetramethyl-1,3,2-dioxaborolan-2-yl)-1H-pyrazole. MS (m/e): 433.5 (M+H)+.

Example 58

Preparation of 1-(2-fluoro-4-(1-methyl-1H-pyrazol-4-yl)benzyl)-N-((1SR,2SR)-2-fluorocyclohexyl)-1H-pyrrolo[3,2-b]pyridine-3-carboxamide

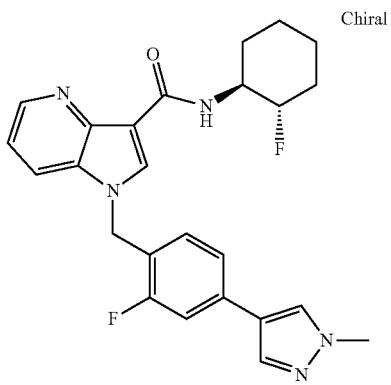 [SMILES: Cn1cc(-c2ccc(Cn3cc(C(=O)N[C@H]4CCCC[C@@H]4F)c4ncccc43)c(F)c2)cn1]

To a suspension of 1-(2-fluoro-4-(1-methyl-1H-pyrazol-4-yl)benzyl)-N-((1SR,2RS)-2-hydroxycyclohexyl)-1H-pyrrolo[3,2-b]pyridine-3-carboxamide (example 37) (40 mg, 89.4 μmol) in 1,2-dichloroethane (800 μl) under nitrogen at 0° C., was added dropwise a solution of bis(2-methoxyethyl)aminosulphur trifluoride (22.9 mg, 19.1 μl, 98.3 μmol) in 1,2-dichloroethane (100 μl). The clear solution was stirred at 0° C. for 2 hours and then allowed to warm to room temperature. The mixture was stirred for 2 hours. The clear solution was cooled in an ice-bath and quenched with a saturated sodium bicarbonate solution keeping the temperature below 10° C. The mixture was diluted with water and dichloromethane. The aqueous layer was separated and extracted twice with dichloromethane. The combined organic layers were dried over sodium sulfate, filtered and concentrated in vacuo. HPLC purification provided 3.2 mg (y: 7.96%) of the title compound as a white solid. MS(m/e): 450.4 (M+H)+.

Example 59

Preparation of 1-[[2-fluoro-4-(1-methylpyrazol-4-yl)phenyl]methyl]-N-[(3R,4S) or (3S,4R)-3-hydroxyoxan-4-yl]pyrrolo[3,2-b]pyridine-3-carboxamide

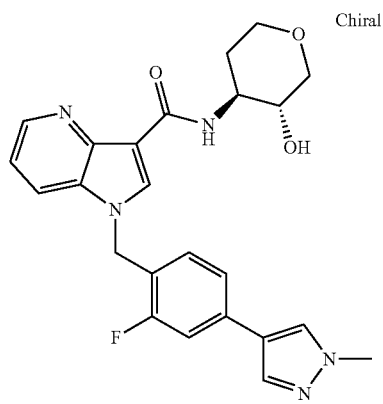 [SMILES: Cn1cc(-c2ccc(Cn3cc(C(=O)N[C@H]4CCOC[C@@H]4O)c4ncccc43)c(F)c2)cn1]

The title compound was prepared by chiral HPLC separation of racemate: 1-(2-fluoro-4-(1-methyl-1H-pyrazol-4-yl)benzyl)-N-((3RS,4SR)-3-hydroxytetrahydro-2H-pyran-4-yl)-1H-pyrrolo[3,2-b]pyridine-3-carboxamide (example 4) on a Reprosil Chiral NR column (second eluting enantiomer, light yellow solid. MS(m/e): 450.5 (M+H)+.

Example 60

Preparation of N-((1S,2S)-2-hydroxycyclohexyl)-1-(4-(thiazol-2-yl)benzyl)-1H-pyrrolo[3,2-b]pyridine-3-carboxamide

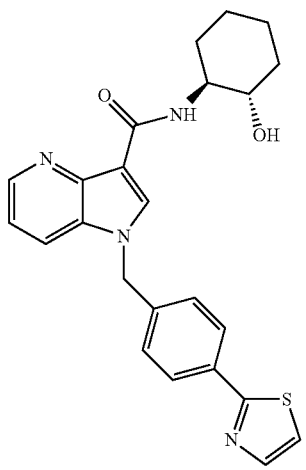 [SMILES: O=C(N[C@H]1CCCC[C@@H]1O)c1cn(Cc2ccc(-c3nccs3)cc2)c2cccnc12]

The title compound was prepared in analogy to example 43 by reacting N-((1S,2S)-2-hydroxycyclohexyl)-1H-pyrrolo

[3,2-b]pyridine-3-carboxamide (example A6) with 2-(4-(chloromethyl)phenyl)thiazole. MS(m/e): 433.3 (M+H)+.

Example 61

Preparation of N-((1S,2S)-2-hydroxycyclohexyl)-1-(4-(methylcarbamoyl)benzyl)-1H-pyrrolo[3,2-b]pyridine-3-carboxamide

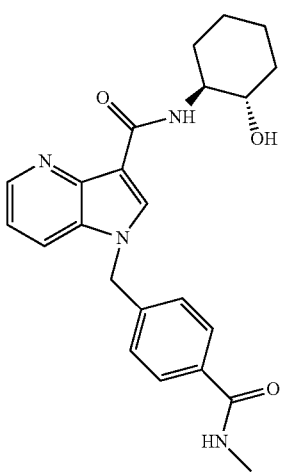 [SMILES: CNC(=O)c1ccc(Cn2cc(C(=O)N[C@H]3CCCC[C@@H]3O)c3ncccc32)cc1]

Step 1: ethyl 4-((3-((1S,2S)-2-hydroxycyclohexylcarbamoyl)-1H-pyrrolo[3,2-b]pyridin-1-yl)methyl)benzoate The title compound was prepared in analogy to example 43 by reacting N-((1S,2S)-2-hydroxycyclohexyl)-1H-pyrrolo[3,2-b]pyridine-3-carboxamide (example A6) with ethyl 4-(bromomethyl)benzoate. MS(m/e): 422.3 (M+H))

Step 2: N-((1S,2S)-2-hydroxycyclohexyl)-1-(4-(methylcarbamoyl)benzyl)-1H-pyrrolo[3,2-b]pyridine-3-carboxamide To a stirred suspension of methanamine hydrochloride (27.9 mg, 413 μmol) at r.t. in 1,4-dioxane (5 ml) under an argon atmosphere was added trimethylaluminum (2 M in toluene; 206 μl, 413 μmol) in one portion. After stirring for 2 hr at r.t., ethyl 4-((3-((1S,2S)-2-hydroxycyclohexylcarbamoyl)-1H-pyrrolo[3,2-b]pyridin-1-yl)methyl)benzoate (58 mg, 138 μmol) was added in one portion. The mixture was heated to 100° C. and stirred overnight. The mixture was cooled to r.t. and treated with H$_2$O (0.5 ml). After stirring for 15 min at r.t., MgSO$_4$ was added, and stirring at r.t. was continued for another 15 min. The mixture was filtered and washed with MeOH. The filtrate was concentrated. The crude product was purified by silica gel chromatography using a CH$_2$Cl$_2$/MeOH gradient as eluent to obtain the title compound (18 mg, 29%) as off-white solid. MS(m/e): 407.3 (M+H)).

Example 62

Preparation of N-((1S,2S)-2-hydroxycyclohexyl)-1-(4-(methylcarbamoyl)benzyl)-1H-pyrrolo[3,2-b]pyridine-3-carboxamide

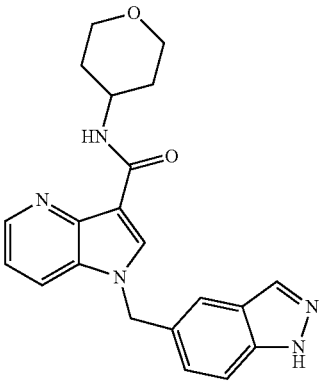 [SMILES: O=C(NC1CCOCC1)c1cn(Cc2ccc3[nH]ncc3c2)c2cccnc12]

The title compound was obtained by reacting N-(tetrahydro-2H-pyran-4-yl)-1H-pyrrolo[3,2-b]pyridine-3-carboxamide (example A.7) with 5-(bromomethyl)-1H-indazole hydrobromide in analogy to the procedure described in example 43. Off-white solid. MS(m/e): 376.2 (M+H)+.

Example 63

Preparation of 1-(4-carbamoylbenzyl)-N-((3S,4R)-3-hydroxytetrahydro-2H-pyran-4-yl)-1H-pyrrolo[3,2-b]pyridine-3-carboxamide and 1-(4-carbamoylbenzyl)-N-((3R,4S)-3-hydroxytetrahydro-2H-pyran-4-yl)-1H-pyrrolo[3,2-b]pyridine-3-carboxamide

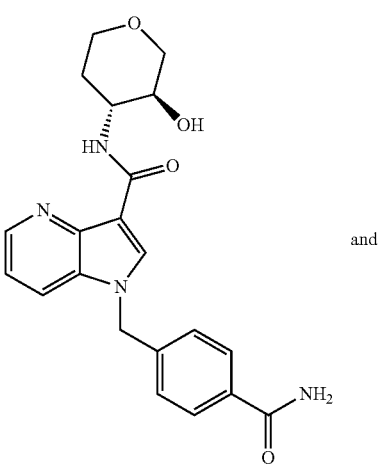

63a and

-continued

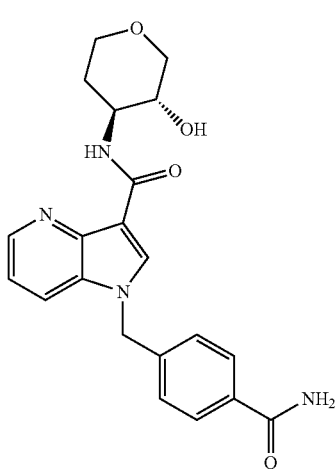

Step 1: 1-(4-Carbamoylbenzyl)-N-((3RS,4SR)-3-hydroxytetrahydro-2H-pyran-4-yl)-1H-pyrrolo[3,2-b]pyridine-3-carboxamide The title compound was prepared in analogy to example 43 by reacting N-[(3RS,4SR)-3-hydroxytetrahydropyran-4-yl]-1H-pyrrolo[3,2-b]pyridine-3-carboxamide (example A.8) with 4-(chloromethyl)-benzamide (CAS 220875-88-7). Colorless solid. MS(m/e): 422.3 (M+H)+

Step 2: 1-(4-Carbamoylbenzyl)-N-((3S,4R)-3-hydroxytetrahydro-2H-pyran-4-yl)-1H-pyrrolo[3,2-b]pyridine-3-carboxamide 63a and 1-(4-carbamoylbenzyl)-N-((3R,4S)-3-hydroxytetrahydro-2H-pyran-4-yl)-1H-pyrrolo[3,2-b]pyridine-3-carboxamide 63b The title compounds were obtained by chiral separation of the racemate in analogy to example 59. Off-white solid with MS(m/e): 395.3 (M+H)+ and off-white solid with 395.2 (M+H)+.

Example 64

Preparation of 1-(2-fluoro-4-(1-methyl-1H-pyrazol-4-yl)benzyl)-N-((1-hydroxycyclopropyl)methyl)-1H-pyrrolo[3,2-b]pyridine-3-carboxamide

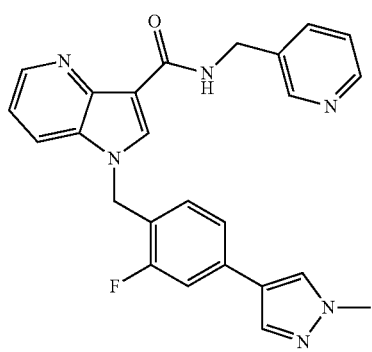 [SMILES: Cn1cc(-c2ccc(Cn3cc(C(=O)NCc4cccnc4)c4ncccc43)c(F)c2)cn1]

In analogy to the procedure described in example 1 the title compound was obtained by coupling intermediate A.2 and pyridin-3-ylmethanamine. White solid. MS(m/e): 441.2 (M+H)+.

Example 65

Preparation of 1-(2-fluoro-4-(1-methyl-1H-pyrazol-4-yl)benzyl)-N-((1-hydroxycyclopropyl)methyl)-1H-pyrrolo[3,2-b]pyridine-3-carboxamide

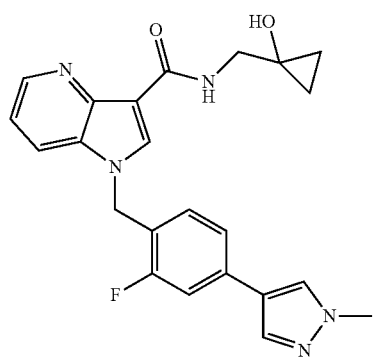 [SMILES: Cn1cc(-c2ccc(Cn3cc(C(=O)NCC4(O)CC4)c4ncccc43)c(F)c2)cn1]

In analogy to the procedure described in example 1 the title compound was obtained by coupling intermediate A.2 and 1-(aminomethyl)cyclopropanol. White foam. MS(m/e): 420.3 (M+H)+.

The invention claimed is:
1. A compound of formula

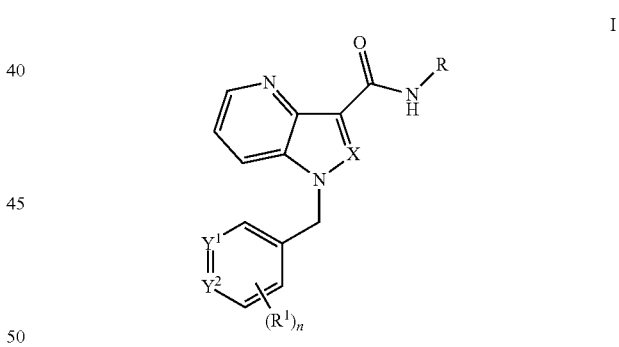

I wherein
R¹ is pyrazolyl, optionally substituted by lower alkyl;
Y¹ is N or CH;
Y² is CH;
and if Y¹ is CH, Y¹ and Y² may form together with the C-atoms to which they are attached a ring, containing —CH═N—N(CH₃)—, —CH═N—N(H)—;
X is CH or N;
R is tetrahydropyran, optionally substituted by hydroxyl; and
L is —CH(CH₂OH)— or —CH₂CH(OH)—;
n is 0, 1 or 2;
m is 0 or 1;
or to a pharmaceutically acceptable acid addition salt, to a racemic mixture or to its corresponding enantiomer and/or optical isomers thereof.

2. A compound selected from the group consisting of:
1-(2-fluoro-4-(1-methyl-1H-pyrazol-4-yl)benzyl)-N-((1S,2S)-2-hydroxycyclohexyl)-1H-pyrrolo[3,2-b]pyridine-3-carboxamide;
1-(2-fluoro-4-(1-methyl-1H-pyrazol-4-yl)benzyl)-N-((1R,2R)-2-hydroxycyclohexyl)-1H-pyrrolo[3,2-b]pyridine-3-carboxamide;
1-[2-fluoro-4-(1-methyl-1H-pyrazol-4-yl)-benzyl]-1H-pyrrolo[3,2-b]pyridine-3-carboxylic acid ((1R,2R)-2-hydroxy-cyclopentyl)-amide;
1-[2-fluoro-4-(1-methyl-1H-pyrazol-4-yl)-benzyl]-1H-pyrrolo[3,2-b]pyridine-3-carboxylic acid ((1S,2S)-2-hydroxy-cyclopentyl)-amide;
1-[2-fluoro-4-(1-methyl-1H-pyrazol-4-yl)-benzyl]-1H-pyrrolo[3,2-b]pyridine-3-carboxylic acid ((1S,2R)-2-hydroxy-cyclopentyl)-amide;
1-[2-fluoro-4-(1-methyl-1H-pyrazol-4-yl)-benzyl]-1H-pyrrolo[3,2-b]pyridine-3-carboxylic acid (1-hydroxy-cyclopentylmethyl)-amide;
N-cyclohexyl-1-(2-fluoro-4-(1-methyl-1H-pyrazol-4-yl)benzyl)-1H-pyrrolo[3,2-b]pyridine-3-carboxamide;
(1-(2-fluoro-4-(1-methyl-1H-pyrazol-4-yl)benzyl)-N-((1SR,2RS)-2 hydroxycyclohexyl)-1H-pyrrolo[3,2-b]pyridine-3-carboxamide;
1-[2-fluoro-4-(1-methyl-1H-pyrazol-4-yl)-benzyl]-1H-pyrrolo[3,2-b]pyridine-3-carboxylic acid ((1S,2S)-2-methoxy-cyclohexyl)-amide;
1-(2-fluoro-4-(1-methyl-1H-pyrazol-4-yl)benzyl)-N-((1SR,2SR)-2-hydroxy-2-methylcyclohexyl)-1H-pyrrolo[3,2-b]pyridine-3-carboxamide;
1-(2-fluoro-4-(1-methyl-1H-pyrazol-4-yl)benzyl)-N-((1SR,2RS)-2-hydroxy-2-methylcyclohexyl)-1H-pyrrolo[3,2-b]pyridine-3-carboxamide;
N-((1S,2S)-2-hydroxycyclohexyl)-1-(3-(1-methyl-1H-pyrazol-4-yl)benzyl)-1H-pyrrolo[3,2-b]pyridine-3-carboxamide;
N-((1S,2S)-2-hydroxycyclohexyl)-1-(4-(1-methyl-1H-pyrazol-4-yl)benzyl)-1H-pyrrolo[3,2-b]pyridine-3-carboxamide;
1-(2-fluoro-4-(1-methyl-1H-pyrazol-4-yl)benzyl)-N-((1SR,2SR)-2-fluorocyclohexyl)-1H-pyrrolo[3,2-b]pyridine-3-carboxamide;
N-((1S,2S)-2-hydroxycyclohexyl)-1-(4-(thiazol-2-yl)benzyl)-1H-pyrrolo[3,2-b]pyridine-3-carboxamide;
1-(5-bromo-2-fluorobenzyl)-N-((1S,2S)-2-hydroxycyclohexyl)-1H-pyrrolo[3,2b]pyridine-3-carboxamide (1S,2S)-2-aminocyclohexanol;
N-((1S,2S)-2-hydroxycyclohexyl)-1-(4-methylbenzyl)-1H-pyrrolo[3,2-b]pyridine-3-carboxamide;
1-(3-fluoro-4-methoxybenzyl)-N-((1S,2S)-2-hydroxycyclohexyl)-1H-pyrrolo[3,2-b]pyridine-3-carboxamide;
1-(4-cyanobenzyl)-N-((1S,2S)-2-hydroxycyclohexyl)-1H-pyrrolo[3,2-b]pyridine-3-carboxamide;
1-(3-fluoro-4-methylbenzyl)-N-((1S,2S)-2-hydroxycyclohexyl)-1H-pyrrolo[3,2-b]pyridine-3-carboxamide;
N-((1S,2S)-2-hydroxycyclohexyl)-1-(4-methoxybenzyl)-1H-pyrrolo[3,2-b]pyridine-3-carboxamide;
1-(biphenyl-4-ylmethyl)-N-((1S,2S)-2-hydroxycyclohexyl)-1H-pyrrolo[3,2-b]pyridine-3-carboxamide;
1-(4-bromobenzyl)-N-((1S,2S)-2-hydroxycyclohexyl)-1H-pyrrolo[3,2-b]pyridine-3-carboxamide;
1-(4-cyano-2-fluorobenzyl)-N-((1S,2S)-2-hydroxycyclohexyl)-1H-pyrrolo[3,2-b]pyridine-3-carboxamide;
1-(4-chlorobenzyl)-N-((1S,2S)-2-hydroxycyclohexyl)-1H-pyrrolo[3,2-b]pyridine-3-carboxamide;
N-((1S,2S)-2-hydroxycyclohexyl)-1-(4-(methylcarbamoyl)benzyl)-1H-pyrrolo[3,2-b]pyridine-3-carboxamide.

3. A compound of formula I according to claim 1, wherein the compound is selected from the group consisting of:
1-(2-fluoro-4-(1-methyl-1H-pyrazol-4-yl)benzyl)-N-((3RS,4SR)-3-hydroxytetrahydro-2H-pyran-4-yl)-1H-pyrrolo[3,2-b]pyridine-3-carboxamide;
1-[[2-fluoro-4-(1-methylpyrazol-4-yl)phenyl]methyl]-N-[(3S,4S)-4-hydroxyoxan-3-yl]pyrrolo[3,2-b]pyridine-3-carboxamide;
1-(2-fluoro-4-(1-methyl-1H-pyrazol-4-yl)benzyl)-N-((3R,4R)-4-hydroxytetrahydro-2H-pyran-3-yl)-1H-pyrrolo[3,2-b]pyridine-3-carboxamide; and
1-[[2-fluoro-4-(1-methylpyrazol-4-yl)phenyl]methyl]-N-[(3R,4S) or (3S,4R)-3-hydroxyoxan-4-yl]pyrrolo[3,2-b]pyridine-3-carboxamide.

4. A compound selected from the group consisting of:
rac-1-[2-Fluoro-4-(1-methyl-1H-pyrazol-4-yl)-benzyl]-1H-pyrrolo[3,2-b]pyridine-3-carboxylic acid (2-hydroxy-3-methoxy-propyl)-amide;
1-[2-Fluoro-4-(1-methyl-1H-pyrazol-4-yl)-benzyl]-1H-pyrrolo[3,2-b]pyridine-3-carboxylic acid ((S)-2-hydroxy-1-methyl-ethyl)-amide;
1-[2-Fluoro-4-(1-methyl-1H-pyrazol-4-yl)-benzyl]-1H-pyrrolo[3,2-b]pyridine-3-carboxylic acid ((R)-2-hydroxy-propyl)-amide;
1-[2-Fluoro-4-(1-methyl-1H-pyrazol-4-yl)-benzyl]-1H-pyrrolo[3,2-b]pyridine-3-carboxylic acid ((S)-2-hydroxy-propyl)-amide;
1-[2-Fluoro-4-(1-methyl-1H-pyrazol-4-yl)-benzyl]-1H-pyrrolo[3,2-b]pyridine-3-carboxylic acid (2-hydroxy-2-methyl-propyl)-amide;
1-[2-Fluoro-4-(1-methyl-1H-pyrazol-4-yl)-benzyl]-1H-pyrrolo[3,2-b]pyridine-3-carboxylic acid ((S)-1-hydroxymethyl-propyl)-amide;
1-[2-Fluoro-4-(1-methyl-1H-pyrazol-4-yl)-benzyl]-1H-pyrrolo[3,2-b]pyridine-3-carboxylic acid (1-hydroxymethyl-propyl)-amide;
1-[2-Fluoro-4-(1-methyl-1H-pyrazol-4-yl)-benzyl]-1H-pyrrolo[3,2-b]pyridine-3-carboxylic acid (2-hydroxy-butyl)-amide;
1-[2-Fluoro-4-(1-methyl-1H-pyrazol-4-yl)-benzyl]-1H-pyrrolo[3,2-b]pyridine-3-carboxylic acid ((R)-2,3-dihydroxy-propyl)-amide;
1-[2-Fluoro-4-(1-methyl-1H-pyrazol-4-yl)-benzyl]-1H-pyrrolo[3,2-b]pyridine-3-carboxylic acid ((S)-1-hydroxymethyl-2-methyl-propyl)-amide;
1-[2-Fluoro-4-(1-methyl-1H-pyrazol-4-yl)-benzyl]-1H-pyrrolo[3,2-b]pyridine-3-carboxylic acid (1-hydroxymethyl-butyl)-amide;
1-[2-Fluoro-4-(1-methyl-1H-pyrazol-4-yl)-benzyl]-1H-pyrrolo[3,2-b]pyridine-3-carboxylic acid ((R)-1-hydroxymethyl-2-methyl-propyl)-amide;
1-[2-Fluoro-4-(1-methyl-1H-pyrazol-4-yl)-benzyl]-1H-pyrrolo[3,2-b]pyridine-3-carboxylic acid (1-hydroxymethyl-2-methyl-propyl)-amide;
1-[2-Fluoro-4-(1-methyl-1H-pyrazol-4-yl)-benzyl]-1H-pyrrolo[3,2-b]pyridine-3-carboxylic acid ((S)-1-hydroxymethyl-butyl)-amide;
1-[2-Fluoro-4-(1-methyl-1H-pyrazol-4-yl)-benzyl]-1H-pyrrolo[3,2-b]pyridine-3-carboxylic acid ((S)-1-hydroxymethyl-3-methyl-butyl)-amide;
1-[2-Fluoro-4-(1-methyl-1H-pyrazol-4-yl)-benzyl]-1H-pyrrolo[3,2-b]pyridine-3-carboxylic acid ((1S,2S)-1-hydroxymethyl-2-methyl-butyl)-amide;

1-[2-Fluoro-4-(1-methyl-1H-pyrazol-4-yl)-benzyl]-1H-pyrrolo[3,2-b]pyridine-3-carboxylic acid ((S)-1-hydroxymethyl-2,2-dimethyl-propyl)-amide;

1-[2-Fluoro-4-(1-methyl-1H-pyrazol-4-yl)-benzyl]-1H-pyrrolo[3,2-b]pyridine-3-carboxylic acid (2-hydroxymethyl-phenyl)-amide;

1-[2-Fluoro-4-(1-methyl-1H-pyrazol-4-yl)-benzyl]-1H-pyrrolo[3,2-b]pyridine-3-carboxylic acid (3-hydroxymethyl-pyridin-2-yl)-amide;

1-[2-Fluoro-4-(1-methyl-1H-pyrazol-4-yl)-benzyl]-1H-pyrrolo[3,2-b]pyridine-3-carboxylic acid (2-hydroxy-2-phenyl-ethyl)-amide;

1-[2-Fluoro-4-(1-methyl-1H-pyrazol-4-yl)-benzyl]-1H-pyrrolo[3,2-b]pyridine-3-carboxylic acid ((S)-2-hydroxy-1-phenyl-ethyl)-amide;

1-[2-Fluoro-4-(1-methyl-1H-pyrazol-4-yl)-benzyl]-1H-pyrrolo[3,2-b]pyridine-3-carboxylic acid (2-hydroxymethyl-4-methyl-phenyl)-amide;

1-[2-Fluoro-4-(1-methyl-1H-pyrazol-4-yl)-benzyl]-1H-pyrrolo[3,2-b]pyridine-3-carboxylic acid ((S)-2-hydroxy-2-phenyl-ethyl)-amide;

1-[2-Fluoro-4-(1-methyl-1H-pyrazol-4-yl)-benzyl]-1H-pyrrolo[3,2-b]pyridine-3-carboxylic acid (3-methyl-pyridin-2-yl)-amide;

1-[2-Fluoro-4-(1-methyl-1H-pyrazol-4-yl)-benzyl]-1H-pyrrolo[3,2-b]pyridine-3-carboxylic acid (3-hydroxy-pyridin-2-yl)-amide; and 1-(2-fluoro-4-(1-methyl-1H-pyrazol-4-yl)benzyl)-N-((1-hydroxycyclopropyl)methyl)-1H-pyrrolo[3,2-b]pyridine-3-carboxamide.

* * * * *